United States Patent
Patzek, IV

(10) Patent No.: US 7,467,890 B2
(45) Date of Patent: Dec. 23, 2008

(54) PORTABLE CHEMICAL TRANSFER/NEUTRALIZING CONTAINMENT SYSTEM

(75) Inventor: Michael J. Patzek, IV, Quakertown, PA (US)

(73) Assignee: Custom Ultrasonics, Inc., Ivyland, PA (US)

(*) Notice: Subject to any disclaimer, the term of this patent is extended or adjusted under 35 U.S.C. 154(b) by 390 days.

(21) Appl. No.: 11/317,540

(22) Filed: Dec. 23, 2005

(65) Prior Publication Data

US 2007/0102045 A1 May 10, 2007

Related U.S. Application Data

(63) Continuation-in-part of application No. 11/267,666, filed on Nov. 4, 2005.

(51) Int. Cl.
*B01F 15/00* (2006.01)
(52) U.S. Cl. .................... 366/165.1; 137/896; 137/592; 137/602; 422/133
(58) Field of Classification Search ................ 137/212, 137/165.4, 896, 592, 165.1, 602; 422/133; 366/165.4, 165.1
See application file for complete search history.

(56) References Cited

U.S. PATENT DOCUMENTS

| | | | |
|---|---|---|---|
| 349,598 A | 9/1886 | Lippincott | |
| 2,628,744 A | 2/1953 | Mowbray | |
| 3,593,728 A * | 7/1971 | Sauer | 134/96.1 |
| 4,619,072 A | 10/1986 | Privett | |
| 4,676,404 A | 6/1987 | Yamazaki et al. | |
| 5,020,917 A * | 6/1991 | Homan | 366/160.4 |
| 5,299,608 A | 4/1994 | Bosyj | |
| 5,761,069 A | 6/1998 | Weber et al. | |
| 5,893,385 A | 4/1999 | Igarashi | |
| 6,241,809 B1 * | 6/2001 | Hopkins | 95/216 |
| 6,341,628 B1 | 1/2002 | Burson | |
| 6,435,379 B2 | 8/2002 | Tansley et al. | |
| 6,601,986 B2 * | 8/2003 | Jang et al. | 366/165.2 |
| 6,863,386 B2 * | 3/2005 | Hatada et al. | 347/84 |

* cited by examiner

*Primary Examiner*—Stephen M Hepperle
*Assistant Examiner*—Atif H Chaudry
(74) *Attorney, Agent, or Firm*—Caesar, Rivise, Bernstein, Cohen & Pokotilow, Ltd.

(57) ABSTRACT

A portable disinfectant transfer system for transferring a toxic and/or noxious fluid between a container and a reprocessor reservoir includes a container for containing the fluid, a pump having a conduit for drawing the fluid from the reservoir and expelling the fluid through an opening of the conduit into the container and an opening in the container for receiving a neutralizing chemical into the container simultaneously with the expelling of the fluid from the reservoir into the container to provide a simultaneously introduced neutralizing chemical. The opening of the conduit is positioned to produce a swirling motion of the fluid within the container to mix the simultaneously introduced neutralizing chemical with the fluid while the fluid is expelled into the container. A further pump having a further conduit is provided for drawing the fluid out of the container.

4 Claims, 14 Drawing Sheets

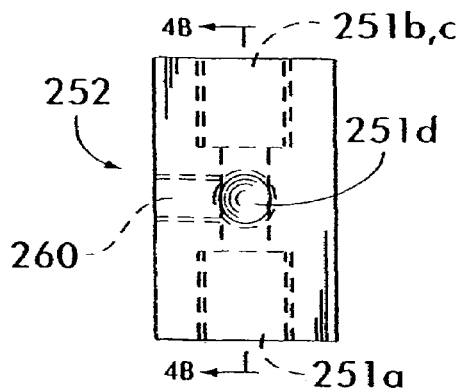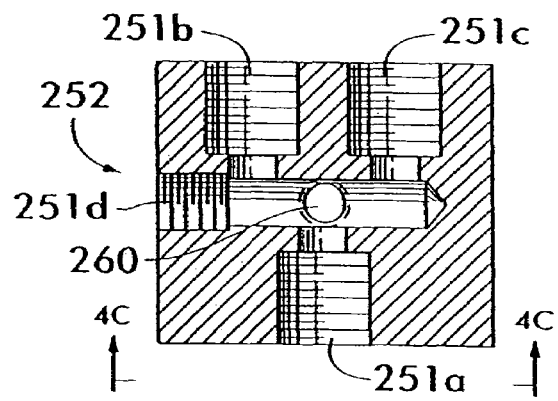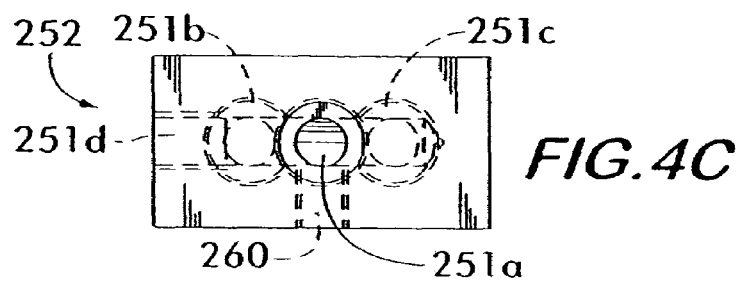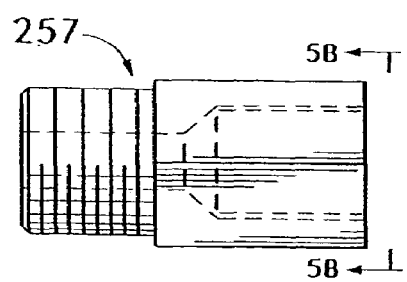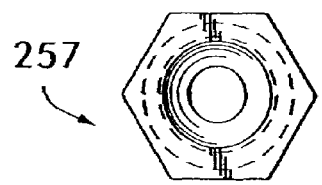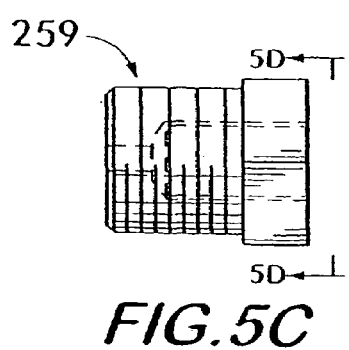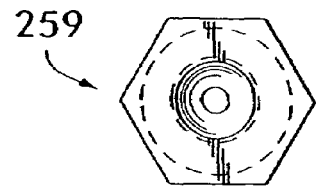

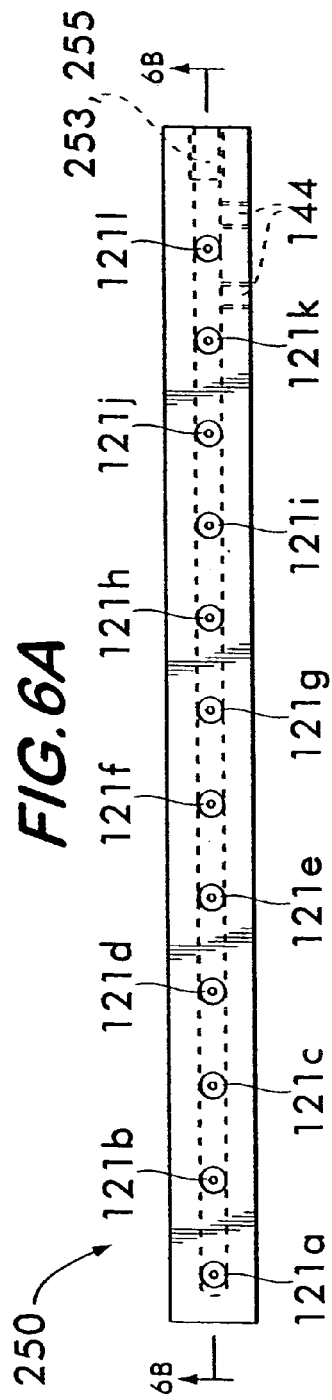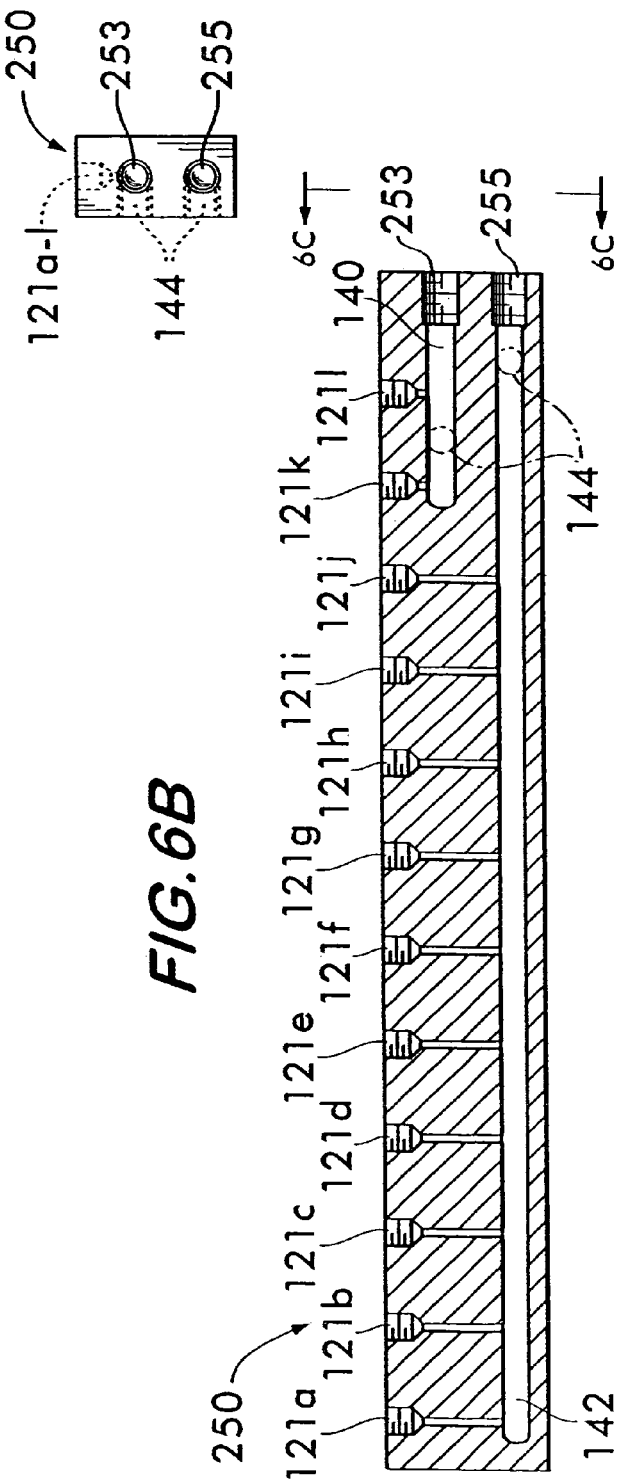

320

320

PORTABLE CHEMICAL TRANSFER/NEUTRALIZING CONTAINMENT SYSTEM

BACKGROUND OF THE INVENTION

1. Field of Invention

This invention relates generally to the transfer of noxious fluids in a system and method for reprocessing a contaminated device having internal passageways before such a device is reused in a clean environment.

2. Description of Related Art

Automated systems for reprocessing devices having internal passageways for reuse are generally available and are commonly relied upon. For example, systems for reprocessing medical instruments having passageways are used by hospitals to safeguard patients and hospital employees from exposure to infection and cross-contamination. Such prior art reprocessing units are manufactured by several different companies including, Custom Ultrasonics, Inc., of Ivyland, Pa., the assignee of the present invention and application. For example, there are reprocessing units in the prior art adapted for cleaning, disinfecting and sterilizing flexible scopes, e.g., upper and lower gastrointestinal scopes, colonoscopes and duodescopes.

The term "reprocessing," as used herein constitutes the washing, disinfecting, sterilizing and/or pasteurizing of such a device. The term "device" as used herein constitutes any devices having internal passageways that require such reprocessing, including, but not limited to, medical instruments and medical devices. The terms "medical instrument" and "medical device" are understood to constitute devices having one passageway or a plurality of passageways, including, but not limited to endoscopes, colonoscopes, and other flexible and rigid medical instruments.

Prior art reprocessing systems, suitable in particular for reprocessing medical instruments, operate in accordance with a predetermined protocol of reprocessing steps. The protocol is based upon the specific cleaning requirements of the particular instruments being cleaned. The reprocessing steps are precisely timed and sequenced in order to assure optimal results, based upon the correct combination of water temperature, detergent and chemical agents. Thus, parameters such as wash and rinse cycle time, chemical immersion cycle time, and water temperature and pressure were preset by the reprocessing unit manufacturer and could not be altered by an end user of the system. U.S. Pat. No. 5,761,069, issued to Weber, et. al., teaches a system for cleaning medical instruments having a database of protocols corresponding to differing medical instruments for permitting a user to load and execute the protocol corresponding to the instrument being reprocessed.

An exemplary protocol for cleaning a medical instrument could include the following reprocessing steps, after the instrument has been placed in the cleaning basin of the reprocessing unit: (1) wash the internal and external surfaces of the instrument with a measured detergent-water mixture for a preset period of time; (2) activate ultrasonic crystals while washing; (3) drain the detergent-water mixture after the wash cycle is completed; (4) after draining, rinse the internal and external surfaces of the instrument with water at a preset temperature for a preset period of time; (5) introduce and circulate disinfectant over and through the instrument for a preset period of time; (6) drain the disinfectant from the wash basin; and (7) after draining of the disinfectant is complete, rinse the instrument with water; and (8) re-rinse the instrument with water.

Prior art reprocessing units adapted, in particular, for reprocessing medical equipment, typically comprise a variety of mechanical components, e.g., pumps, tubes, solenoid valves, ultrasonic transducers, heaters and probes that perform the various reprocessing steps. The pumps used in these units must be very precise and reliable over extended periods of time. Thus, pumps that are suitable for these units can be quite expensive.

In many cases it is necessary to reprocess devices having passageways of differing diameters. The differing diameters can occur in a single device having passageways of differing diameters, or in multiple devices, each having passageways of differing diameters. The presence of differing diameter passageways creates a need for fluid flows of corresponding differing pressures, because more narrow passageways require a higher pressure to force fluid therethrough. Prior art reprocessing units suitable for reprocessing devices having passageways of differing diameters included a plurality of pumps and associated tubing systems, wherein each pump provided one of the differing pressures required to reprocess the differing passageways of the devices.

Furthermore, some devices can have extremely narrow passageways, requiring dedicated high-pressure pumps that are capable of providing extremely high pressures. Pumps for such extremely narrow, high-pressure passageways have very low flow rates. Flow rates that are this low are difficult to monitor. For example, the flow rates of fluids through the passageways of some devices can be on the order of a drop a minute. Passageways this narrow can be found, for example, in flexible medical instruments, such as endoscopes.

Known reprocessing units are typically equipped with a pressure sensor for measuring the overall flow of fluid through the pump for the purpose of detecting obstructions in the passageways of the devices. However, is possible for an obstruction preventing flow of in one of the passageways to go undetected by the pressure sensor since the flow can continue through the remaining passageways and only the overall pressure of the liquid is determined.

Several governmental and independent agencies have issued guidelines for reprocessing particular types of medical instruments. For example, such guidelines often require that certain types of medical instruments be washed and sterilized using a chemical disinfectant, while other types of instruments need only be washed. The design of reprocessing units and the reprocessing steps they perform must conform to such guidelines. Additionally, guidelines have been created to reliably prevent instruments from being reused if an obstruction occurs in a single passageway of a plurality of passageways during reprocessing. Prior art reprocessing units are not reliably able to meet these guidelines.

Chemical disinfectants useful for reprocessing medical instruments or devices include glutaraldehyde or ortho-phthaladehyde (OPA). One particularly effective type of chemical disinfectant is 2% or 3% glutaraldehyde which is marketed by a number of different companies under various brand names such as Cidex manufactured by Johnson & Johnson. However such disinfectants are dangerous to handle because they can cause asthma, headaches, or hives, or maybe be sensitizing or carcinogenic. Typically workers handling such disinfectants pour them into a reservoir where the disinfectant can then be used to reprocess medical instruments or devices. Pouring, however, is disadvantageous because it may result in spilling or splashing of the disinfectant. The spilled or splashed disinfectant may get onto a worker or may fall onto a floor and be missed thereby causing a hazard. Additionally, noxious and/or toxic fumes are given off by the disinfectants when they are poured. Because of the danger such fumes pose they need to be controlled. The fumes are very heavy and tend to fall. Use of a vent overhead of the reservoir would not be useful because it would pull the fumes into a worker's face, and fumes from spilled or splashed disinfectant would likely be missed. Moreover, expensive equipment would be needed for the vent to work since it would have to be articulated to the area of the reservoir.

In addition to pouring, it is also known to pump rather than to displace the chemical disinfectant. However, a problem with pumping the liquid is that not all of it is removed. The push of pump acting on a liquid leaves some liquid in the conduits through which the liquid passes and this liquid will fall back into bottle once the pump is turned off.

While applicant is aware that devices for displacement of liquid with a gas, e.g. air, are known in the prior art, such devices are not suitable for situations in which there is a danger posed by toxic and/or noxious fumes. Nor do such devices involve the transfer of toxic and/or noxious liquid. See for example, U.S. Pat. Nos. 349,598, 2,628,744, 4,619,072, 4,676,404, 5,299,608, 5,893,385, 6,341,628, and 6,435,379.

The present invention would result in essentially no fumes being released when the disinfectant is transferred from a bottle to a reservoir. Thus resulting in increased safety and eliminating any need to exhaust outside.

All references cited herein are incorporated herein by reference in their entireties.

BRIEF SUMMARY OF THE INVENTION

A portable disinfectant transfer system for transferring a toxic and/or noxious fluid between a container and a reprocessor reservoir includes a container for containing the fluid, a pump having a conduit for drawing the fluid from the reservoir and expelling the fluid through an opening of the conduit into the container and an opening in the container for receiving a neutralizing chemical into the container simultaneously with the expelling of the fluid from the reservoir into the container to provide a simultaneously introduced neutralizing chemical. The opening of the conduit is positioned to produce a swirling motion of the fluid within the container to mix the simultaneously introduced neutralizing chemical with the fluid while the fluid is expelled into the container. A further pump having a further conduit is provided for drawing the fluid out of the container. A well at the bottom of the container has an opening of the further conduit positioned within the well to empty the container. Fittings are coupled to the conduit and the further conduit for placing the container into fluid communication with the reprocessor reservoir. The opening of the conduit into the container is an opening of a fitting coupled to the conduit. The fitting coupled to the conduit is positioned within the interior of the container to cause the fluid being expelled from the conduit into the interior of the container to swirl within the container. The fitting coupled to the conduit is positioned within the interior of the container to cause the fluid being expelled from the conduit into the interior of the container to swirl within the container to mix the simultaneously introduced neutralizing chemical with the fluid while the fluid is being expelled into the container.

The fitting coupled to the conduit is positioned at a predetermined distance from the bottom of the container to mix the simultaneously introduced neutralizing chemical with the fluid while the fluid is being expelled into the container. The fitting coupled to the conduit is positioned between approximately five inches and approximately seven inches from the bottom of the container to mix the simultaneously introduced neutralizing chemical with the fluid while the fluid is being drawn into the container. The fitting coupled to the conduit can be positioned at approximately six inches from the bottom of the container to mix the simultaneously introduced neutralizing chemical with the fluid while the fluid is being drawn into the container. The fitting coupled to the conduit is positioned at a predetermined angle with respect to the bottom of the container to mix the simultaneously introduced neutralizing chemical with the fluid while the fluid is being drawn into the container. The fitting coupled to the conduit is positioned at an angle between approximately twenty degrees and approximately forty degrees with respect to the bottom of the container to mix the simultaneously introduced neutralizing chemical with the fluid while the fluid is being drawn into the container. The fitting coupled to the conduit is positioned at an angle of approximately thirty degrees with respect to the bottom of the container to mix the simultaneously introduced neutralizing chemical with the fluid while the fluid is being drawn into the container.

A method for maintaining a reprocessor unit having a reservoir containing a toxic and/or noxious fluid includes providing a portable container for containing the fluid coupled to a vehicle for transporting the portable container to the vicinity of the reprocessor unit and pumping the fluid from the reservoir and expelling the fluid into the portable container through an opening using a pump coupled to the vehicle. An operation is performed upon the reprocessor and the fluid from the portable container is pumped to the reservoir after the operation is performed using a pump coupled to the vehicle. A neutralizing chemical is introduced into the container simultaneously with the expelling of the fluid into the portable container to provide a simultaneously introduced neutralizing chemical. The opening is positioned to produce a swirling motion of the fluid within the portable container to mix the simultaneously introduced neutralizing chemical with the fluid while the fluid is expelled into the container. The opening is positioned between approximately five inches and approximately seven inches from the bottom of the container to mix the simultaneously introduced neutralizing chemical with the fluid.

BRIEF DESCRIPTION OF SEVERAL VIEWS OF THE DRAWINGS

The invention will be described in conjunction with the following drawings in which like reference numerals designate like elements and wherein:

FIGS. 4A-C show top, front and plan views of the pressure differentiation device of the reprocessing unit of FIG. 2.

FIGS. 5A-D show front and side views of the pressure control devices of the pressure differentiation manifold of FIGS. 4A-C.

FIGS. 6A-C show top, front and plan views of the pressure distribution manifold of a system for reprocessing of a device.

DETAILED DESCRIPTION OF THE INVENTION

Figure 1:
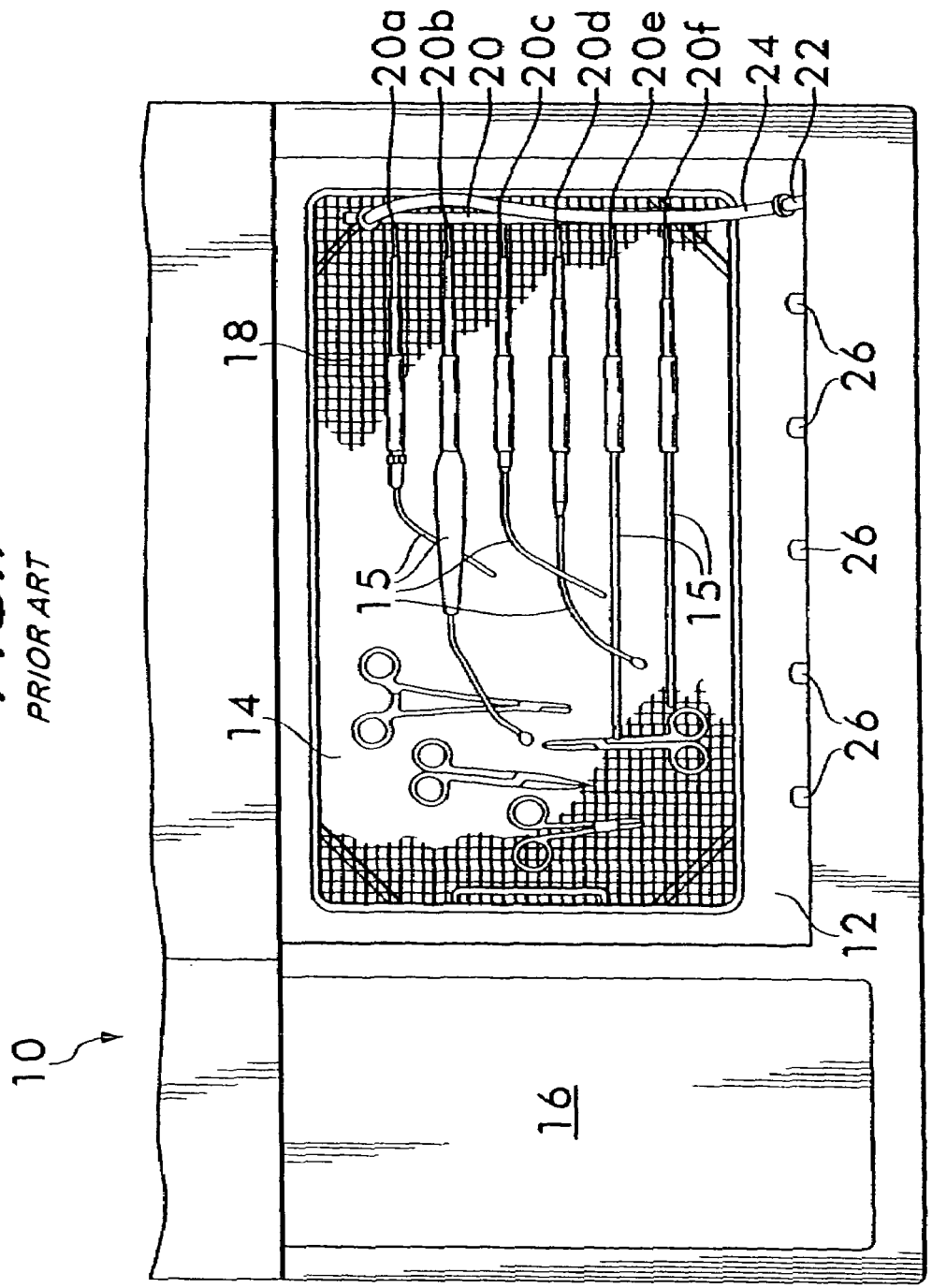
FIG. 1 is a top plan view of a prior art reprocessing unit wherein the cover of the reprocessing unit is disposed in an opened position to permit a view of a reprocessing basin containing devices to be reprocessed.

Referring now to the drawings, wherein like reference numerals refer to like parts, there are shown representations of reprocessing systems and methods suitable for using conventional reprocessing protocols to reprocess devices having internal passageways, such as medical instruments. An example of such a reprocessing protocol is disclosed in U.S. Pat. No. 5,761,069, issued to Weber, et. al., which is incorporated by reference herein.

FIG. 1 shows a top view of a prior art reprocessing unit 10, wherein a cover (not shown) is disposed in an open position. The reprocessing unit 10 includes a reprocessing basin 12, the instrument carrier 14, and a chemical disinfectant reservoir 16. The instrument carrier 14 is shown seated within the reprocessing basin 12. The instrument carrier 14 can be generally rectangular in shape and comprises a mesh-like bottom 18 which is arranged to hold the surgical instruments 15 during reprocessing, wherein the surgical instruments 15 each include a single passageway therethrough requiring reprocessing. The reprocessing basin 12 is also provided with a plurality of spray nozzles 26 for use during the rinse cycle.

The instrument carrier 14 includes a manifold assembly 20 having a plurality of ports 20a-f, each of which is shown applied to an internal passageway of a respective surgical instrument 15. In order to reprocess the surgical instruments 15 having a single passageway within the reprocessing unit 10, the surgical instruments 15 are disposed on the instrument carrier 14 for coupling to the ports 20a-f. Since the surgical instruments 15 have a single passageway, only a single one of the ports 20a-f is required for each surgical instrument 15. The manifold assembly 20 is connected to a port 22 by means of a tubing segment 24, which conducts fluid flow from the port 22 to the manifold assembly 20 for distribution by way of the ports 20a-f.

The fluid flow of the port 22 is driven by an oscillating pump (not shown). The oscillating pump operates to draw fluid, e.g., wash water, rinse water or chemical disinfectant, from the reprocessing basin 12, circulate that fluid through the ports 20a-f and the manifold assembly 20, and through the respective passageways of the surgical instruments 15 disposed on the instrument carrier 14, to effect the decontamination process during the wash, rinse and chemical immersion phases of the reprocessing protocol.

In this manner, the pressure delivered to each of the passageways of the surgical instruments 15 can be substantially equal in the reprocessing unit 10. Reprocessing unit 10 is thus suitable for reprocessing a plurality of surgical instruments 15 requiring such a single pressure to be applied to all of the passageways of the surgical instruments 15. However, many surgical instruments are provided with passageways of differing diameters. Such surgical instruments require differing pressures, corresponding to the differing diameters, for providing the required circulation of wash water, rinse water and chemical disinfectants through the passageways.

Figure 2:
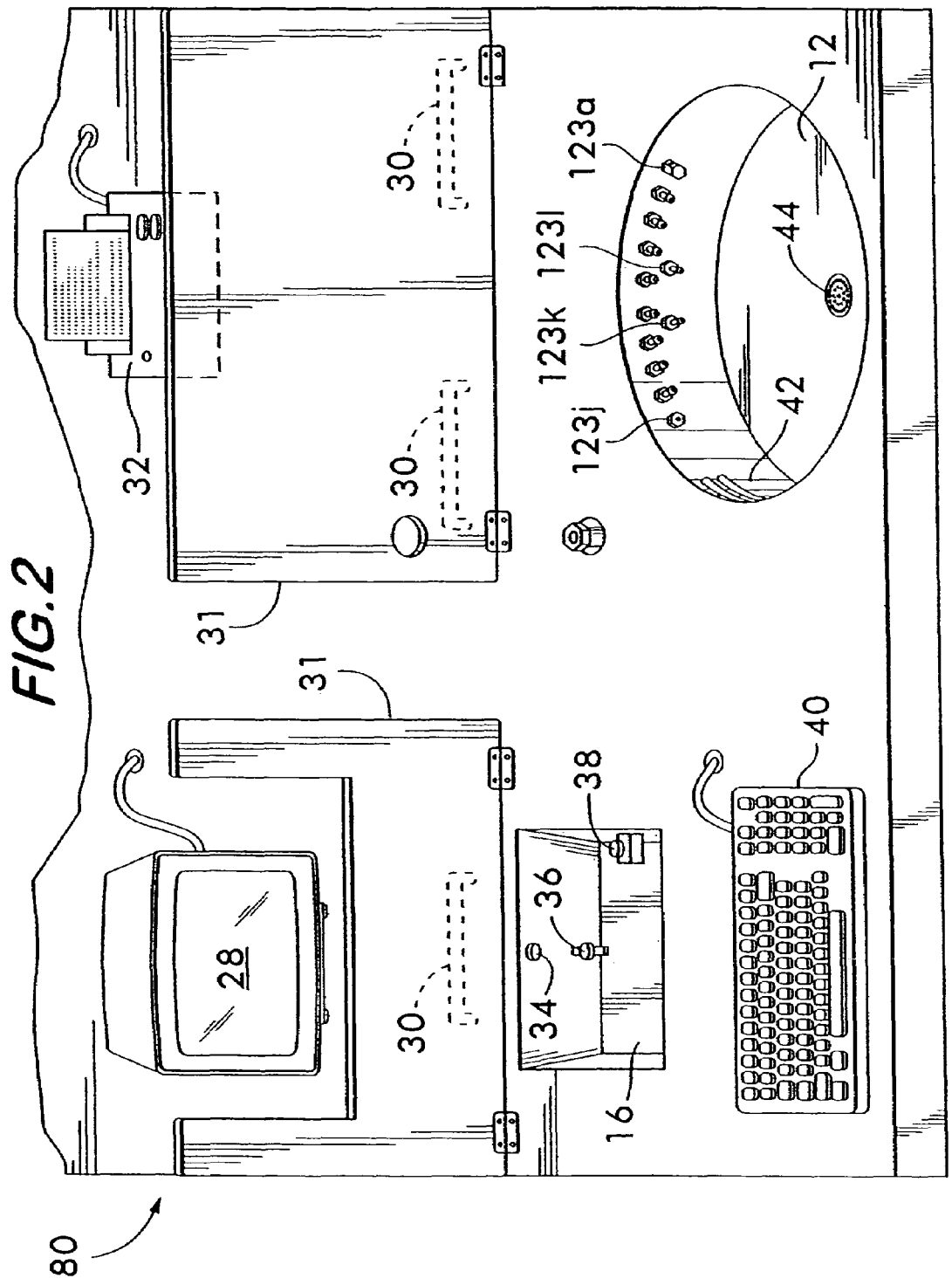
FIG. 2 is an elevational view of a reprocessing unit suitable for use with the system and method for reprocessing of a device.
Figure 3:
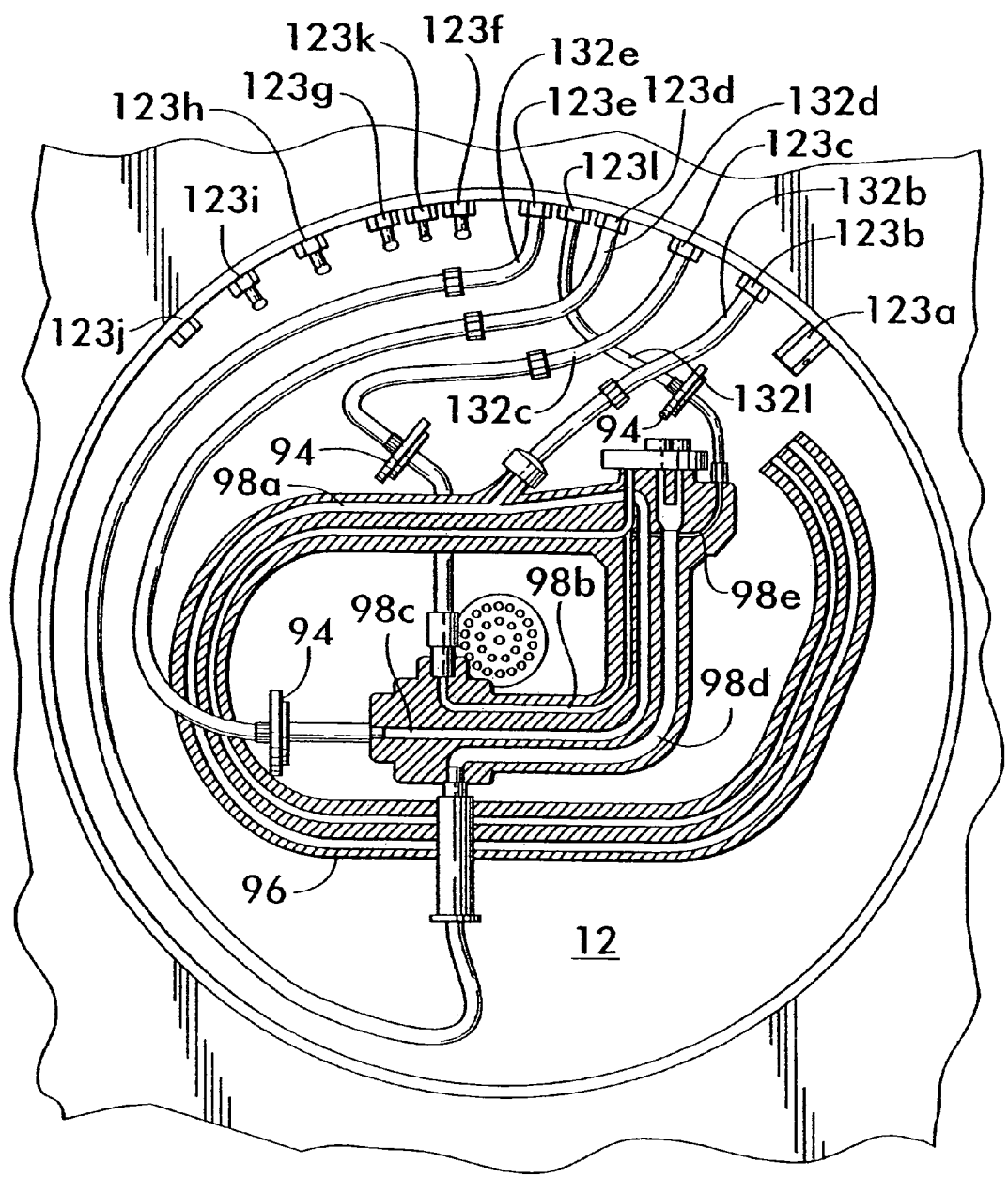
FIG. 3 shows a top view of the reprocessing basin of the reprocessing unit of FIG. 2 including a device to be reprocessed.

Referring now to FIGS. 2, 3, there is shown a reprocessing unit 83 suitable for use with the system and method for reprocessing of a device, and a view of a reprocessing basin 12 within the reprocessing unit 83. The reprocessing basin 12 holds a device 96 having internal passageways 98a-e for reprocessing of the device 96 by the reprocessing unit 83. In a preferred embodiment, the device 96 being reprocessed by the reprocessing unit 83 can be a medical instrument 96. In particular, the system and method for reprocessing of a device are well suited for application to medical instruments including flexible scopes such as endoscopes that are used for upper and lower gastrointestinal studies.

The reprocessing unit 83 includes a keyboard 40, a monitor 28, a printer 32, and an associated personal computer (not shown) for permitting a user of the reprocessing unit 83 to communicate with and control the reprocessing unit 83. The reservoir 16 of the reprocessing unit 83 includes the sensors 34, 36, 38 for controlling devices such as a heater, a pump and a vacuum device (not shown) in order to protect against failure conditions such as overflow conditions in the reservoir 16. A removable door 42 within the reprocessing basin 12 covers additional sensors (not shown) for providing further operational capability and safety protection during the operation of the reprocessing unit 83. The door stops 30 are provided to stop the motion of the rotatable doors 31 covering the reservoir 16 and the reprocessing basin 12 when they are opened.

In the preferred embodiment, the reprocessing basin 12 can hold more than one device 96 upon a mesh for reprocessing of the internal passageways 98a-e thereof according to conventional reprocessing protocols. The reprocessing unit 83 is adapted to provide fluid flows of differing pressures to the device 96 or devices 96 being reprocessed when the internal passageways 98a-e have differing diameters. The reprocessing unit 83 is adapted to perform the multi-pressure reprocessing operations using a single pump (not shown), and to provide an indication of an obstruction in any of the internal passageways 98a-e of the device or devices 96 as described in more detail below. The single pump of the reprocessing unit 83 can be a diaphragm pump, an oscillating pump, or any other type of pump known to those skilled in the art. Alternatively, the reprocessing unit 83 can be adapted to perform the multi-pressure reprocessing operations using more than one pump. These pumps could supply pressurized fluid flows of differing pressures to the inputs ports 253, 255 of the pressure distribution manifold 250.

The reprocessing basin 12 includes the supply ports 123a-l that can be selectively used to apply fluids at different fluid flow rates to the medical instruments 96 for reprocessing of the medical instruments 96. For example, the supply port 123j can be capped and reserved for use when needed. The supply port 123a can be used to blow off a fluid flow which is unusable due to difficulty in regulating and measuring their flow rates, as described in more detail below. In this example, at least the supply ports 123a-l that are not capped or blown off can be vented into the reprocessing basin 12 or coupled to the internal passageways 98a-e of a medical instrument 96 as needed For example, an internal biopsy passageway 98a of the medical instrument 96 can be coupled to the supply port 123b by way of the tubing segment 132b, and an internal water channel passageway 98b of the medical instrument 96 can be coupled to the supply port 123c by way of the tubing segment 132c. The internal passageway 98c can be coupled to the supply port 123d by way of the tubing segment 132d, and the internal suction passageway 98d can be coupled to the supply port 123e by way of the tubing segment 132e. The internal elevator water channel passageway 98e can be coupled to the supply port 123l by way of the tubing segment 132l.

The fluid applied in the reprocessing method can be either liquid or gas. Gases that are used for the reprocessing of a medical device include, but are not limited to, ethylene oxide, hydrogen peroxide, and plasma gases.

The disk filters 94 and their tubing extensions can be disposed in line with the selected passageways 98a-e for preventing debris from reaching the medical instrument 96. For example, the disk filters 94 can be provided in the tubing segments 132c,d,e. The device for coupling the selected tubing segments 132a-l to the tubing extensions of the disc filters as shown can be the well known lure lock type of coupling. Typical diameters for some of the passageways 98a-e can be 0.508 millimeters to 4.8 millimeters.

Referring now to FIGS. 4A-C, there is shown a pressure differentiation device 252 for providing fluid flows of differing pressures from the output of a single conventional pump that provides a single pump output pressure. It is the different output pressures at the output of the pressure differentiation device 252 that are applied by way of the selected supply ports 123a-l to the internal passageways 98a-e of the medical instrument 96 for reprocessing the medical instrument 96 or any other device 96 having such passageways 98a-e. The single pump applied to the pressure differentiation device 252 can be a conventional diaphragm type pump, an oscillating pump, or any other type of pump known to those skilled in the art. The pressure differentiation device 252 can be a conventional T-manifold that is known to those skilled in the art.

The single pump output pressure is applied to the pressure differentiation device 252 at an input port 251a for application to the two output ports 251b,c of the pressure differentiation device 252. The output ports 251b,c threadably receive and secure different pressure control devices which can have openings of different diameters, as described in more detail below. The pressure control devices secured in the output ports 251b,c permit the pressure differentiation device 252 to provide two different pressures for the internal passageways 98a-e of the medical instruments 96. In the preferred embodiment the output port 251b can be a high pressure output port and the output port 251c can be a low pressure output port.

In a typical embodiment, the higher pressure of the high pressure output port 251b of the pressure differentiation device 252 can be approximately 25 to 50 pounds per square inch. The lower pressure of the low pressure output port 251c can be approximately 2 to 20 pounds per square inch. The pressures at the output ports 251b,c can fluctuate within these ranges depending on factors such as the number of medical instruments 96 coupled to the reprocessing unit 83. It will be understood by those skilled in the art that a pressure differentiation device 252 having additional output ports with different pressure control devices can be used for reprocessing systems 83 requiring more than two differing pressures.

Referring now to FIGS. 5A-D, there are shown the pressure control devices 257, 259 of the pressure differentiation device 252 for providing the two different pressures to the internal passageways 98a-e of the medical instrument 96. The pressure control devices 257, 259 can be conventional pressure control orifice fittings 257, 259 that are threadably received and secured in the output ports 251b,c of the pressure differentiation device 252. The two different pressures are provided at the output ports 251b,c when a single pressure is applied to the input port 251a of the pressure differentiation device 252 because of the different diameters of the openings within the pressure control orifice fittings 257, 259. The pressure control orifice fitting 257 is a high pressure orifice fitting and the pressure control orifice fitting 259 is a low pressure orifice fitting.

In the preferred embodiment, the pressure differentiation device 252 can be formed with an entrance 260 for permitting an FDA approved liquid chemical sterilant as well as alcohol to be injected into the fluid stream passing through the device 252 for transmission through the selected supply ports 123a-l of the reprocessing basin 12 to the medical instruments 96. A disinfectant injection bulkhead communicating with the entrance 260 can be located on the exterior of the reprocessing unit 83 for convenience. Additionally, a filter (not shown) can be disposed in a conduit from the pump to the input port 251a of the device 252 for filtering fluid in transit to the internal passageways 98a-e. The filter can be, for example, a one-hundredth micron filter.

Referring now to FIGS. 6A-C, there are shown representations of the pressure distribution manifold 250 of the reprocessing unit 83, including the manifold input ports 253, 255, and the manifold output ports 121a-l. The pressure distribution manifold 250 can be a conventional air manifold understood by those skilled in the art. It is adapted to receive the fluid flows of the two different pressures from the output ports 251b,c of the pressure differentiation device 252 by way of the manifold input ports 253, 255. The fluid flows from the pressure distribution manifold 250 are applied by way of the manifold output ports 121a-l directly to the corresponding supply ports 123a-l of the reprocessing unit basin 12. Therefrom, they are selectively applied to the devices 96 such as the medical instruments 96. In the preferred embodiment, the manifold output ports 121a-j are low pressure ports and the manifold output ports 121k,l are high pressure ports.

A high pressure fluid flow is received at the high pressure manifold input port 253 of the pressure distribution manifold 250 from the orifice port 251b of the pressure differentiation device 252. A short longitudinal bore hole 140, opening at the high pressure manifold input port 253, is provided at one end of the pressure distribution manifold 250. The pressure distribution manifold 250 is bored transversely from each of the high pressure manifold output ports 121k,l to the longitudinal high pressure bore hole 140 in order to permit the high pressure output ports 121k,l to communicate with the high pressure bore hole 140. Thus, a high pressure fluid flow applied to the input port 253 of the pressure distribution manifold 250 is distributed to the high pressure, or narrower inner diameter, passageways of the medical instruments 96 by way of the high pressure bore hole 140 and the manifold output ports 121k,l.

A low pressure fluid flow is received at the low pressure input port 255 of the pressure distribution manifold 250 from the output port 251c of the pressure differentiation device 252. A long longitudinal bore hole 142, opening at the low pressure manifold input port 255, is provided within the pressure distribution manifold 250. Substantially as described with respect to the high pressure output ports 121k,l, transverse bore holes extending from the low pressure output ports 121a-j to the longitudinal low pressure bore hole 142 are provided. Thus, the low pressure manifold output ports 121a-j communicate with the low pressure bore hole 142. In this manner, a low pressure fluid flow applied to the low pressure input port 255 of the pressure distribution manifold 250 is distributed to the low pressure passageways of the medical instruments 96 byway of the low pressure bore hole 142 and the manifold output ports 121*a-j*.

Those skilled in the art will understand that possible turbulence at the distal end of the pressure distribution manifold 250, in the region of the manifold output port 121*a* can make the flow rates difficult to measure and/or difficult to control. Therefore, in the preferred embodiment, the fluid flows provided by way of the supply port 123*a* can be blown off into the reprocessing basin 12, rather than applied to a medical instrument 96.

The pressure measurement openings 144 on the side of the pressure distribution manifold 250 individually communicate with the longitudinal bore holes 140, 142. The presence of the pressure measurement openings 144 on the pressure distribution manifold 250 permits measurement of the pressures within the bore holes 140, 142, as described in more detail below.

Figure 7:
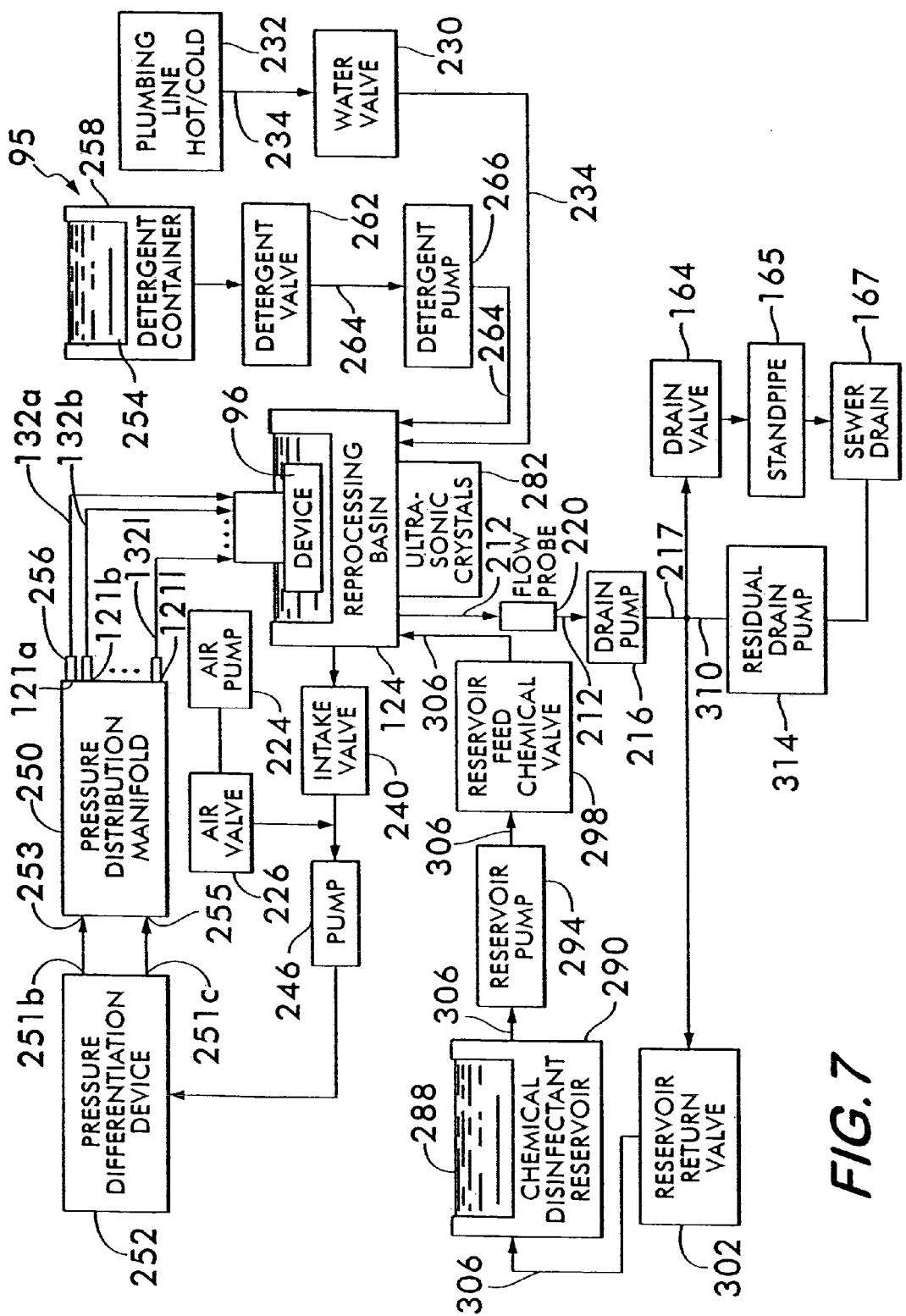
FIG. 7 shows a schematic block diagram illustrating the process flow of the operations performed by the reprocessing unit of FIG. 2.

Referring now to FIG. 7, there is shown a block diagram representation of a process flow 95 for performing a reprocessing protocol within the reprocessing unit 83 suitable for reprocessing devices such as the medical instruments 96. During a fill step of the process flow 95, a solenoid-type water valve 230 is placed in an open position to enable water to flow from an outside hot/cold water source 232 through a water line 234, into the reprocessing basin 12 to immerse the medical instrument 96. The reprocessing basin 12 is provided with a drain 44 (shown in FIG. 2) located in the bottom of the reprocessing basin 12. The drain 44 is connected to a drain line 212. During the fill step, as wash water flows into the reprocessing basin 12 it begins to drain through the drain line 212. A drain valve 164, provided below the drain line 212 is normally in a closed state to prevent the draining of the water out of the system. This action enables the filling of the reprocessing basin 12.

A flow probe 220 is located adjacent the drain line 212 and is operative to detect the presence of liquid as wash water begins to fill the drain line 212 during filling of the reprocessing basin 12. Once the probe 220 detects the presence of moisture, the probe 220 sends a signal indicative thereof to a system controller which provides an indication to the user that the reprocessing basin 12 is filling with water. Additionally, an operational float (not shown) is located within the reprocessing basin 12. During filling, the operational float is buoyed upwardly and eventually reaches a predetermined height corresponding to a particular volume of wash water being present in the reprocessing basin 12. When the operational float reaches this predetermined level, the reprocessing unit 83 indicates to the user that the reprocessing basin 12 has been filled and that the washing step can begin. Thereafter, the water valve 230 is closed so that no additional wash water enters the reprocessing basin 12.

As wash water fills into the reprocessing basin 12 over the immersed medical instruments 96, a solenoid-type detergent valve 262 and a detergent pump 266 operate to withdraw a predetermined amount, e.g., three ounces, of detergent 254 from a detergent container 258 located adjacent the reprocessing unit 83 and inject the predetermined amount of detergent into the reprocessing basin 12 through a detergent line 264. The detergent 254 may be of any suitable composition. One particularly effective type of detergent is sold under the trademark TERGAL 800 by Custom Ultrasonics, Inc.

During the wash step, a pump 246, such as a diaphragm pump, is activated to draw the water/detergent mixture contained in the reprocessing basin 12 through an intake valve 240 and to circulate the mixture through the circular reprocessing basin 12, the output ports 121*a-l* of the pressure distribution manifold 250, the tubing segments 132*a-l*, and through the internal passageways 98*a-e* of the immersed medical instrument 96. Any unused output ports 121*a-l* can be blown off into the basin 12. The pump 246 is a single output pressure pump. In this manner fluid is recirculated through the immersed medical instrument 96 for a predetermined period of time in order to reprocess the internal passageways of the internal medical instrument 96 in accordance with a predetermined reprocessing protocol.

Figure 8A:
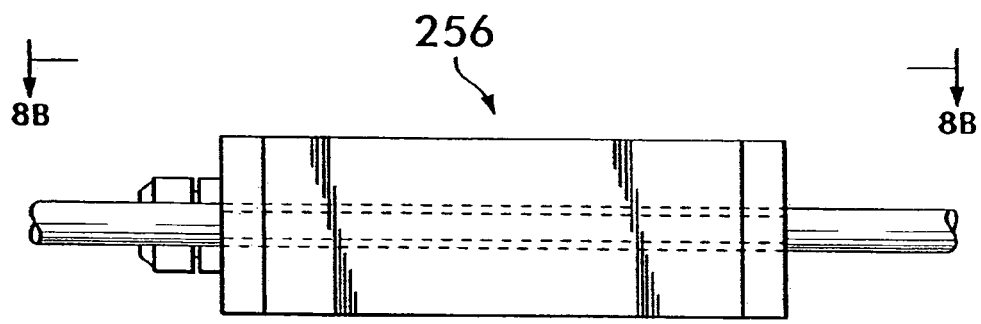
FIGS. 8A-B show top and front views of a flowmeter of a system for reprocessing of a device.
Figure 8B:
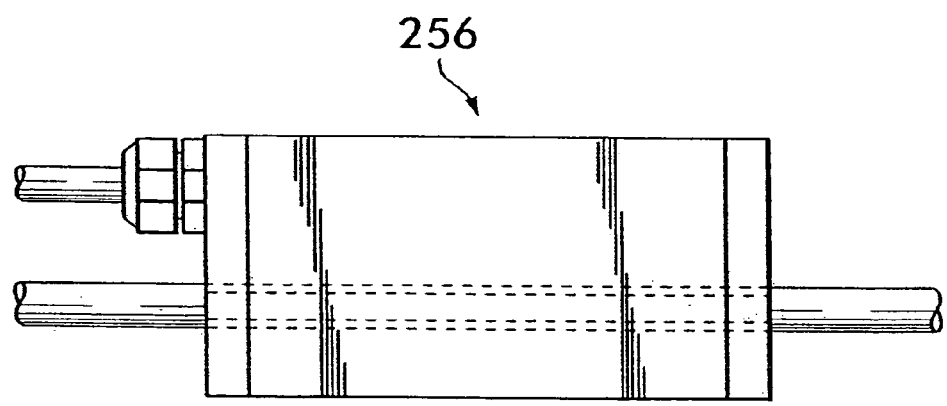

Referring now to FIGS. 8A-B, there is shown a flowmeter 256 for selectively coupling to the manifold output ports 121*a-l* and individually measuring the flow rates of the fluids within the manifold output ports 121*a-l* of the reprocessing unit 83 coupled thereto. The flowmeter 256 can be any conventional flow sensor suitable for measuring the flow rate through the ports 121*a-l*, and thereby through the tubing segments 132*a-l*. For example, the flowmeter 256 can be an in line straight-through flow tube sensor that uses ultrasonic sensing technology to measure the rate of flow of a fluid passing therethrough, such as the M-1500 Series provided by Malema Flow Sensors. The flowmeter 256 can be omitted from any unselected output ports 121*a-l* not supplying fluid to any internal passageways, for example the output ports 121*a* which is blown off into the reprocessing basin 12.

An ultrasonic sensing flowmeter 256 is preferred because it is non intrusive, thereby permitting the fluid flow to the internal passageways 98*a-e* of the medical instruments 96 to be measured without interference by the flowmeter 256. Ultrasonic sensing flowmeters 256 of this type are believed to be accurate from one-half cubic centimeter per minute to infinity for a multiple number of outputs.

The flowmeter 256 provides a flow rate signal according to the measured flow rate, for example by tripping a switch within the flowmeter 256 when the flow rate falls below a predetermined value.

In another embodiment, the flowmeters 256 can be of the well know piston type, wherein the force of the fluid flow through the flowmeter 256 raises and suspends a piston therein, until the flow rate falls below a predetermined value. When the flow rate falls below the predetermined value, the piston falls and a switch within the flowmeter 256 is tripped. The tripping of the switch within the flowmeter 256 indicates that the predetermined flow rate through the flowmeter 256 has not been maintained. It is believed that a flowmeter 256 of this type is not as accurate the ultrasonic type since it can interfere with the fluid flow being measured.

In one preferred embodiment, the minimum flow rate through the high pressure ports 121*k,l* can be approximately one cubic centimeter per minute. The minimum flow rate through the two lower pressure ports 121*a,b* at the distal end of the pressure distribution manifold 250 can be approximately fifty cubic centimeters per minute. The minimum flow rate through the remaining low pressure ports 121*c-j* can be 0.05 gallons per minute.

Thus, the flowmeters 256 disposed in line with the internal passageways 98*a-e* provide an indication to the user of the reprocessing system 83 when the flow through any of the passageways 98*a-e* of the surgical instruments 96 coupled to the reprocessing unit 83 is obstructed. When any of the internal passageways 98*a-e* is determined to be obstructed in this manner, the reprocessing operation set forth in the process flow 95 is aborted, and the abort condition is communicated to the user of the reprocessing unit 83. This feature prevents the inadvertent reuse of any device 96 that has not been completely reprocessed due to an obstruction in any of the internal passageways 98*a-e* being reprocessed. Without such a feature the operator can be left with a false sense of security regarding the success of the reprocessing operation.

In the preferred embodiment, individual indicator lights (not shown) corresponding to each flowmeter 256 coupled to the pressure distribution manifold 250 are mounted on the exterior of the reprocessing unit 83. The indicator lights permit an easy visual determination of which internal passageway 98a-e is obstructed when the reprocessing operation is aborted. Additionally, in one preferred embodiment, a lag time of approximately ten seconds can be provided between the detection of an obstruction by a flowmeter 256 and the abort of the reprocessing operation to allow for the breaking up of an obstruction due to back pressure provided by the pump.

Figure 9A:
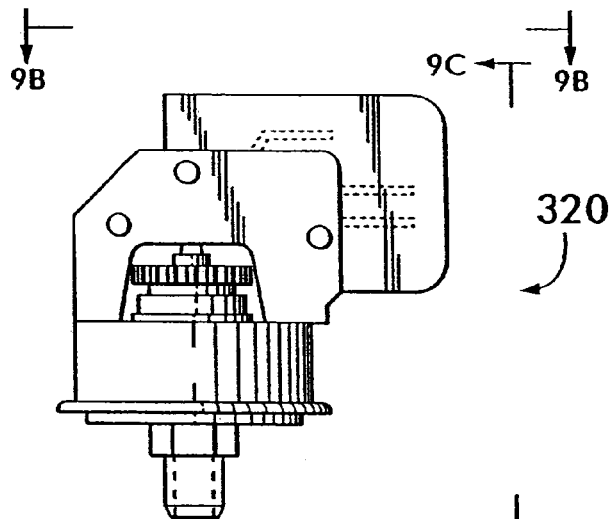
FIGS. 9A-C show top, front and plan views of a pressure sensor of a system for reprocessing of a device.
Figure 9B:
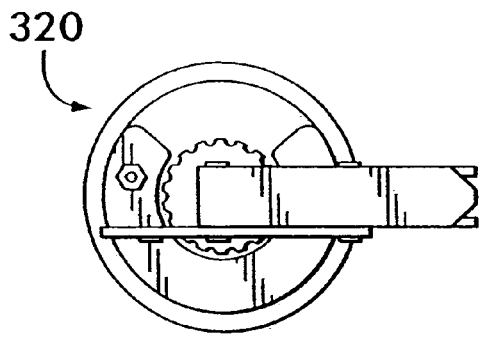
Figure 9C:
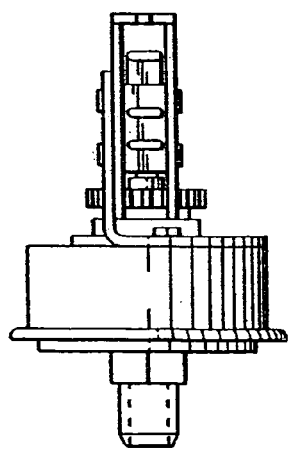

Referring now to FIGS. 9A-C, there are shown representations of the pressure sensing switch 320 of the reprocessing unit 83. The pressure sensing switch 320 is adapted to measure the pressure of the longitudinal bore holes 140, 142 within the pressure distribution manifold 250, and to provide an electrical pressure signal according to the measured pressure of the bore holes 140, 142.

In an alternate embodiment (not shown) a flowmeter 256 coupled to a manifold output port 121a-l of the pressure distribution manifold 250 can be omitted. In such an embodiment, the pressure sensing switch 230 is mounted in a pressure measurement opening 144 communicating with a longitudinal bore 140, 142 of the pressure distribution manifold 250. For example, the flowmeters 256 can be removed from the manifold output ports 121k,l, and the high pressure flow rate can be measured by a pressure sensing switch 320 mounted in the pressure measurement opening 144 disposed in communication with the longitudinal bore hole 140.

Thus, the pressure of the manifold output ports 121k,l is monitored using the pressure sensing switch 320 rather than measuring the fluid flow rate using a flowmeter 256. In this alternate embodiment, an obstruction within a high pressure passageway of the medical instrument 96 is detected by sensing a change in pressure rather than a change in flow rate. Thus, the reprocessing of the instrument 96 is aborted according to the pressure measured by the pressure sensing switch 320 rather than a direct measurement of flow rate. In one embodiment the pressure sensing switch 320 can be adapted to provide an electrical pressure signal when the measured pressure is at a level in the range of 1.5 to 15 psi.

Figure 10:
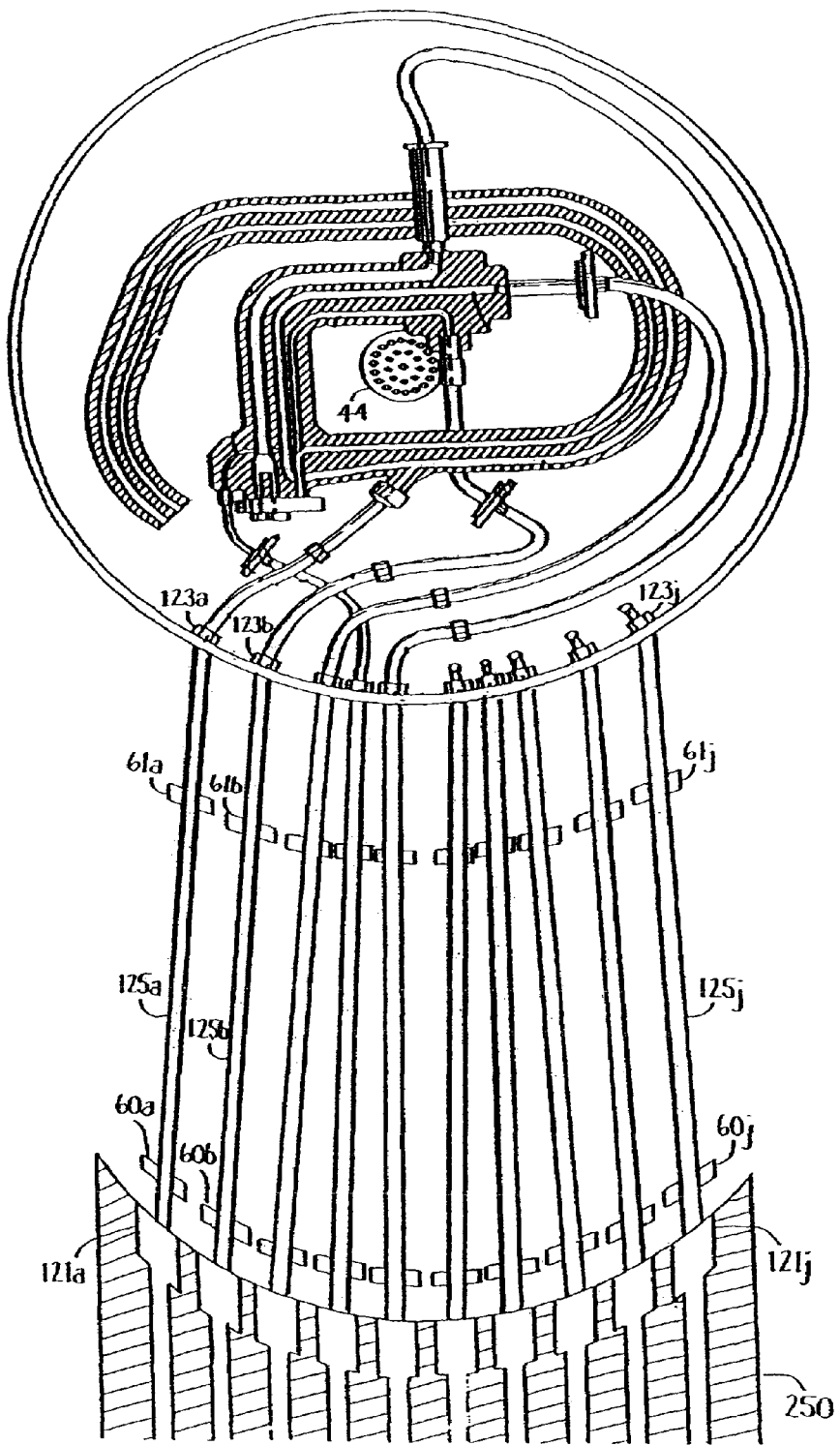
FIG. 10 shows a top view of an embodiment of a system for reprocessing of a device, with a distribution manifold with pressure sensors mounted at two points of the flow path on each output port of the distribution manifold.

Referring now to FIG. 10, there is shown a portion of the reprocessing unit 350. The reprocessing unit 350 is an alternate embodiment wherein the flow paths 125a-j transmit fluid from the manifold output ports 121a-j of the distribution manifold 250 to the supply ports 123a-j. The flow paths 125a-j can be, for example, tubing segments. Each flow path 125a-j is provided with two pressure sensors 60a-j, 61a-j. The two pressure sensors 60a-j, 61a-j of each flow path 125a-j are spaced apart and mounted at two points on each of the flow paths 125a-j. The flowmeters 256 can be omitted in this embodiment, as flow is monitored using the pressure sensors 60a-j, 61a-j. In a preferred embodiment, the pressure sensors 60a-j, 61a-j will measure two pressure values for each output port 121a-j. These values can then be used to determine the flow rates through the flow paths 125a-j. This calculation can easily be performed by one skilled in the art. For example, the two pressures can be applied to the well-known Bernoulli equation to calculate the flow through the output ports 121a-j.

Preferably, the pressure sensors 60a-j, 61a-j should be positioned not to obstruct or restrict the flow path. This will ensure a more accurate pressure reading. Additionally, in a preferred embodiment the flow through the flow paths 125a-j should be as close to laminar as possible. This also will increase the accuracy of the pressure readings. Preferably, the distribution manifold 250 is designed to achieve laminar flow.

In this embodiment, the reprocessing of the instrument or device 96 is aborted according to the flow rate determined from the two measured pressures on each output port 121a-j. Preferably, signals representing the pressure values detected by the pressure sensors 60a-j, 61a-j are transmitted to a computer equipped with software designed to process the signals. The software will translate the pressure values into flow rates, for example, by using the Bernoulli equation. When the pressure differential signifies no flow or minimum flow, according to predetermined minimum flow levels, the cycle is aborted.

The reprocessing unit can include a plurality of pumps (not shown) and associated tubing systems 132a-l, wherein each pump provides one of the differing pressures required to reprocess the differing passageways of the devices 96. Each individual tube of the tubing assembly can have its flow monitored separately by flow determining sensors on each tube. The flow determining sensors can be pressure sensors, or flow meters (piston type or ultrasonic).

In another embodiment, the reprocessing unit can include individual pumps (not shown) associated with each individual flow path 125a-j. The single pump 246 with the pressure differentiation device 252 would be omitted, as well as the pressure distribution manifold 250. In this embodiment, the fluid is pulled from within the reprocessing basin 124, through the purge intake filter 240, feeding the inputs of the individual pumps (not shown). Each pump then supplies a flow path 125a-j, for example tubing segments, to the supply ports 123a-j located on the reprocessing basin 124 at a predetermined flow and/or pressure rate. This predetermined flow and/or pressure rate is monitored separately by flow determining sensors. The flow determining sensors can be pressure sensors, or flow meters (piston type or ultrasonic).

In the preferred embodiment, individual indicator lights (not shown) corresponding to each pair of pressure sensors 60a-j, 61a-j mounted to the pressure distribution manifold 250 are mounted on the exterior of the reprocessing unit. The indicator lights permit an easy visual determination of which internal passageway 98a-e is obstructed when the reprocessing operation is aborted. Additionally, in one preferred embodiment, an adjustable lag time can be provided between the detection of an obstruction by the pressure differential and the abort of the reprocessing operation to allow for the breaking up of an obstruction due to back pressure provided by the pump.

In another alternate embodiment (not shown) of the reprocessing unit 83 an ultrasonic flow sensor such as the flowmeter 256 can be mounted on the pressure distribution manifold 250, for example, at the input end of the pressure distribution manifold 250. This type of ultrasonic measurement of flow rate is extremely sensitive, allowing the detection of changes in flow rate as small as a few drops per minute. The reprocessing operations of the process flow 95 are aborted when the flow detected by such an ultrasonic measurement device mounted on the pressure distribution manifold 250 in this manner is below the predetermined level.

Once the water/detergent mixture has passed through the internal passageways 98a-e of the immersed medical instrument 96, it flows back into the reprocessing basin 12 where it is again recirculated by the pump 246 for a predetermined minimum period of time based upon guidelines provided by the detergent manufacturer, e.g., one-hundred eighty seconds. During the wash step, the ultrasonic crystals 282 located below the reprocessing basin are activated. When activated, the ultrasonic crystals 282 generate ultrasonic vibrations that act in combination with the detergent-water mixture to cause a cleansing action that breaks down, loosens and removes contaminants from the exterior and interior surfaces of the flexible medical instrument 96 to provide enhanced cleaning.

Once the predetermined time period for the wash step has elapsed, the drain step begins. During the drain step, the drain valve 164 is opened and the drain pump 216 is activated. While the pump 246 continues to pump the water/detergent mixture through the medical instrument 96, the mixture begins to drain out of the reprocessing basin 12 by means of the drain pump 216 which pumps the water/detergent mixture down the drain line 212 and into a T-assembly 217. The mixture travels through drain valve 164, through a standpipe 165 and into a sewer drain 167. Once the flow probe 220 detects the absence of moisture in the drain line 212, the drain pump 216 is shut off and the drain valve 164 is returned to its closed position.

After the drain pump 216 is shut off, an air pump 224 is activated and a solenoid-type air valve 226 is opened. By use of the air pump 224 forced air is directed through the pump 246, the manifold assembly 250, the tubing segments 132*a-e*, and through the internal channels of the medical instrument 96. The forced air acts to purge and clear away any residual water/detergent mixture remaining in the interior channels of the medical instrument 96. The purged residual water/detergent mixture flows down the drain line 212 located below the reprocessing basin 12 and collects in the bottom of the T-assembly 217 located below the drain line 212. The purged residual water/detergent mixture is removed from the bottom of the T-assembly 217 by means of a residual drain line 310 and a residual drain pump 314 that is activated simultaneously with the air pump 224.

The first rinse cycle comprises the steps of fill, rinse and drain steps. During the fill step, water is introduced into the reprocessing basin 12 from the outside source 232 by means of water valve 230 and water line 234. Since this is a rinse cycle, as opposed to a wash cycle, no detergent 254 is introduced during the fill step. During the rinse step of the process flow 95, the pump 246 draws the rinse water contained in the reprocessing basin 12 through the intake valve 240 and recirculates the rinse water for a predetermined minimum period of time in a manner as previously described above in connection with the wash step. Also, during the rinse step, the ultrasonic crystals 282 are activated.

Thereafter, the drain step begins. During the drain step, rinse water is pumped out of the reprocessing basin 12 by the drain pump 216. The water travels down the drain line 212 through the drain pump 216 and into the T-assembly 217. Because the drain valve 164 is in the opened position, the water travels through drain valve 164 and through standpipe 165 and into a sewer drain 167.

Once the flow probe 220 detects the absence of moisture in the drain line 212, the drain pump 216 is shut off. Some residual water remains in the bottom of the T-assembly 217 that cannot be removed by the drain pump 216. This residual rinse water is removed from the bottom of the T-assembly 217 by means of the residual drain line 310 and the residual drain pump 314 in the manner previously described. By removing all residual rinse water from the T-assembly 217, chemical disinfectant introduced in the next step of the protocol will not become diluted with any residual rinse water.

Once the drain step 141 is complete and all residual rinse water has been removed from the T-assembly 217, the next fill step begins and a chemical disinfectant 288 is introduced into the reprocessing basin 12. One particularly effective type of chemical disinfectant is 2% or 3% glutaraldehyde which is marketed by a number of different companies under various brand names such as Cidex manufactured by Johnson & Johnson. The introduction of the disinfectant 288 is effected by opening a reservoir feed valve 298 to cause a reservoir pump 294 to pump the chemical disinfectant 288 from a chemical disinfectant reservoir 290 through a chemical line 306 into the reprocessing basin 12. The chemical disinfectant 288 enters and fills the reprocessing basin 12 to a predetermined height as previously described.

Once the reprocessing basin 12 has been filled with the chemical disinfectant 288 to the predetermined level, the pump 246 is activated to draw the chemical disinfectant 288 contained in the reprocessing basin 12 through the intake valve 240. This action circulates the chemical disinfectant 288 through the ports of the manifold 250, the tubing segments 132*a-e* and through the internal passageways 98*a-e* of the immersed medical instrument 96. Once the chemical disinfectant 288 has passed through the internal passageways of 98*a-l* of the immersed medical instrument 96, it flows back into the reprocessing basin 12 where it is recirculated by the pump 246 for a predetermined minimum period of time based upon guidelines provided by the manufacturer of the chemical disinfectant 288. Once the predetermined minimum time period for the chemical immersion step has elapsed, the pump 246 is turned off.

Thereafter, the chemical disinfectant 288 is returned to the chemical disinfectant reservoir 290 for reuse. To enable the return of the chemical disinfectant 288 to the reservoir 290, the drain valve 164 is closed and the reservoir return valve 302 is opened. The drain pump 216 is activated and the chemical disinfectant 288 is pumped through the chemical line 306, through the reservoir return valve 302 and back into the chemical reservoir 290. Once the flow probe 220 detects the absence of moisture in the drain line 212, the drain pump 216 is tuned off. Thereafter, two additional rinse cycles are performed. The first rinse cycle comprises a first rinse and a drain phase. The rinse cycle is performed in a manner similar to the rinse cycle previously described. However, this rinse cycle does not include use of the residual drain line 310 and residual drain pump 314. The ultrasonic crystals 282 are activated during the rinse step of this rinse cycle.

The second rinse cycle comprises fill, second rinse and drain phases. This rinse cycle is performed in a manner similar to the rinse cycle previously described, i.e., fill, rinse and drain phases, and includes use of the residual drain line 310 and residual drain pump 314. The ultrasonic crystals 282 are activated during the rinse step of this rinse cycle. Once this rinse cycle has been completed, the reprocessing protocol is complete and the instrument may be removed from the reprocessing chamber for reuse.

Figure 11:
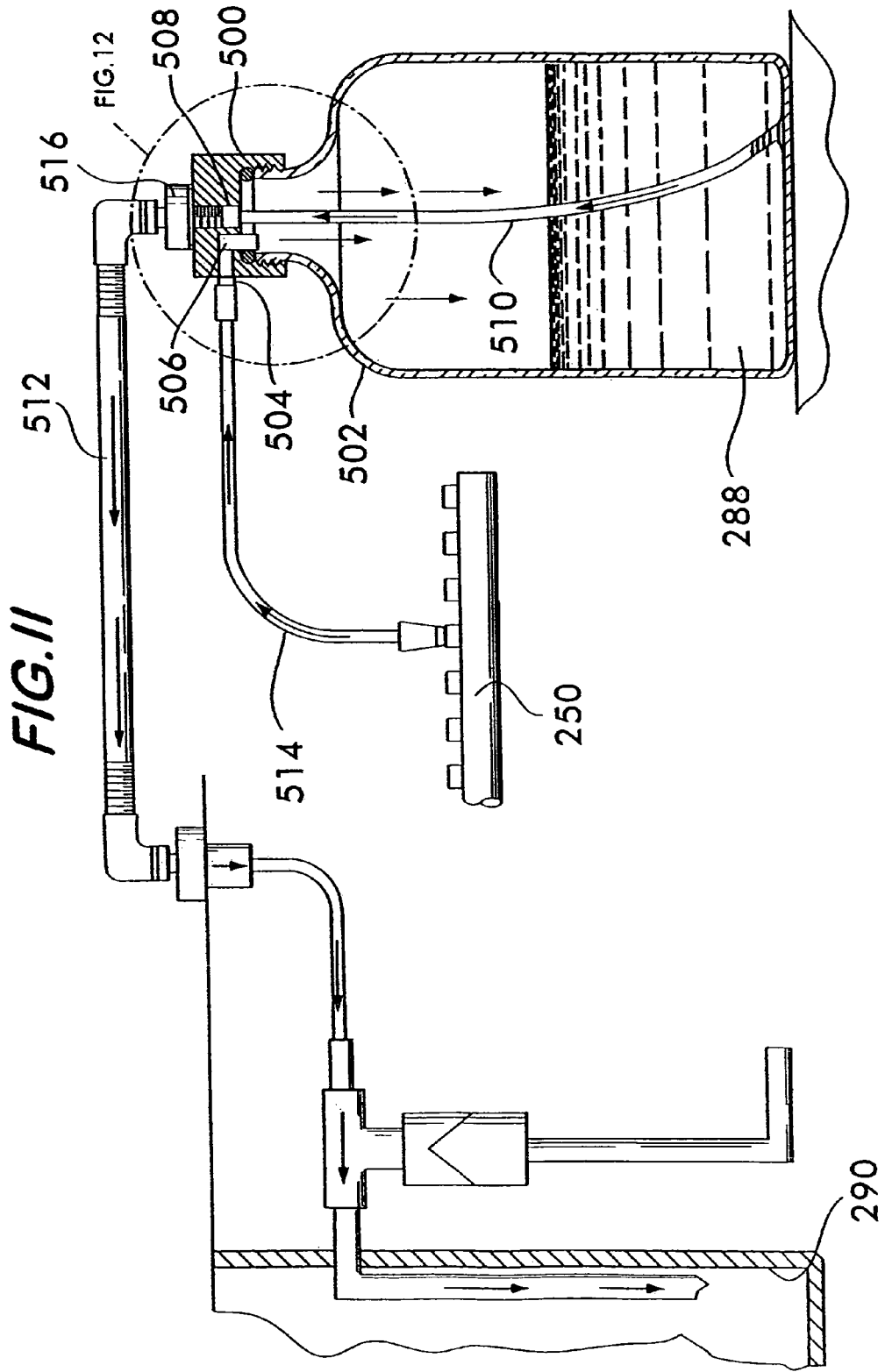
FIG. 11 is a view of a disinfectant transfer system according the present invention.
Figure 12:
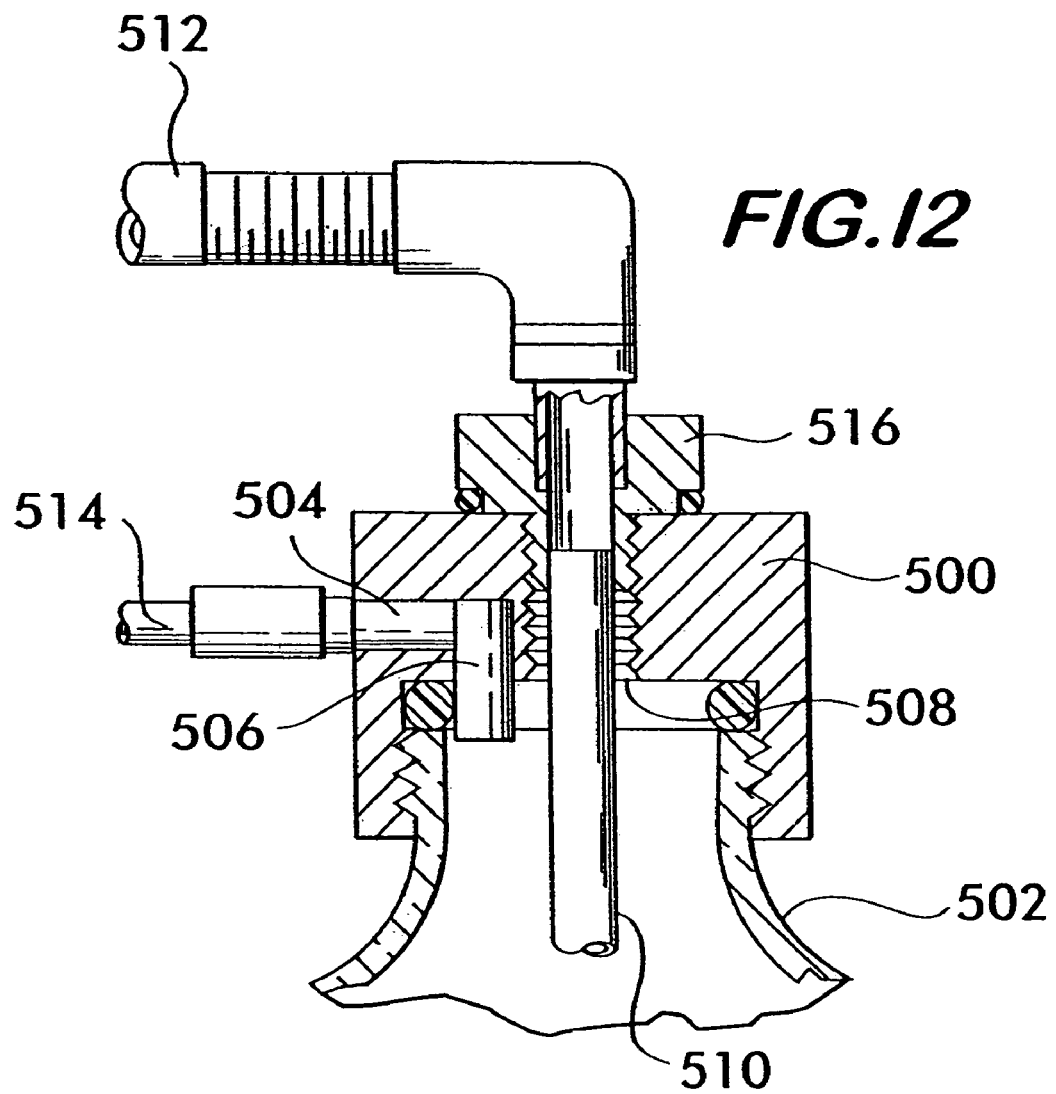
FIG. 12 is a cross-sectional blow-up view of the transfer cap shown in FIG. 11 according to the present invention.

Referring now to FIGS. 11 and 12, there is shown a disinfectant transfer system according to the invention. A transfer cap 500 is fitted onto a bottle 502 containing a chemical disinfectant 288. The transfer cap 500 has a first opening 504 for letting air, or some other gas, in through a valve 506 which is inserted in the first opening 504. A second opening 508 on the transfer cap 500 is provided for allowing the chemical disinfectant 288 to exit the bottle 502 when the chemical disinfectant 288 is displaced by air entering through the valve 506 in the first opening 504. Preferably the valve 506 is a spring loaded self-closing locking valve of a type well known to those skilled in the art. A first conduit 510 connected to the bottom of the second opening 508 and extending to the bottom of the bottle 502, allows for a pathway by which the chemical disinfectant 288 can exit the bottle 502. From the first conduit 510 the chemical disinfectant can then enter a second conduit 512, which is connected to the top of the second opening 508, and flow into a reservoir 290 into which the chemical disinfectant 288 can enter.

In a preferred embodiment, a manifold 250 linked to the first opening 504 by a third conduit 514 can be used to supply the air which enters the bottle 502 through the first opening 504. However, any source of air can be used. Additionally, in a preferred embodiment an o-ring 516 is fitted between the second opening 508 and the second conduit 512 to assist in creating an essentially vapor tight seal. Still furthermore, in a preferred embodiment the valve 506 is a one-way check valve for only allowing air to enter the bottle 502.

It should be appreciated that the disinfectant transfer system described is a closed system from inside of the bottle, or other suitable container, to inside of the reservoir. Therefore, essentially no fumes escape during the transfer of the disinfectant from the bottle to the reservoir.

If should further be appreciated that the transfer cap detachably attaches onto the bottle, or other suitable container, and can therefore be removed and detachably attached onto another bottle, or other suitable container. As a result, disinfectant contained in multiple bottles, or other suitable containers, can be easily transferred to a reservoir through the closed system.

Figure 13:
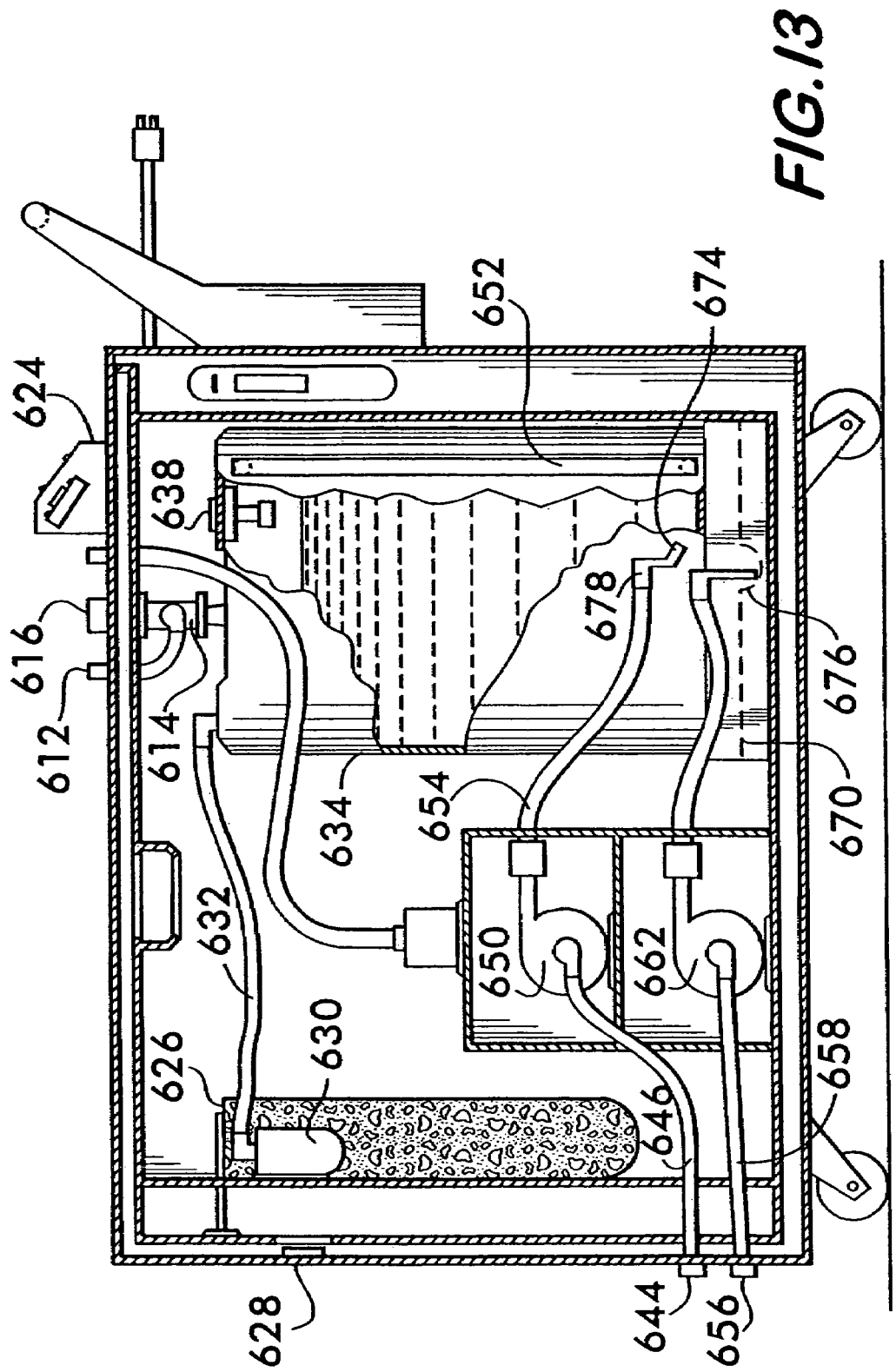
FIG. 13 is a cross-sectional side view of the chemical neutralizing station of the present invention.
Figure 14:
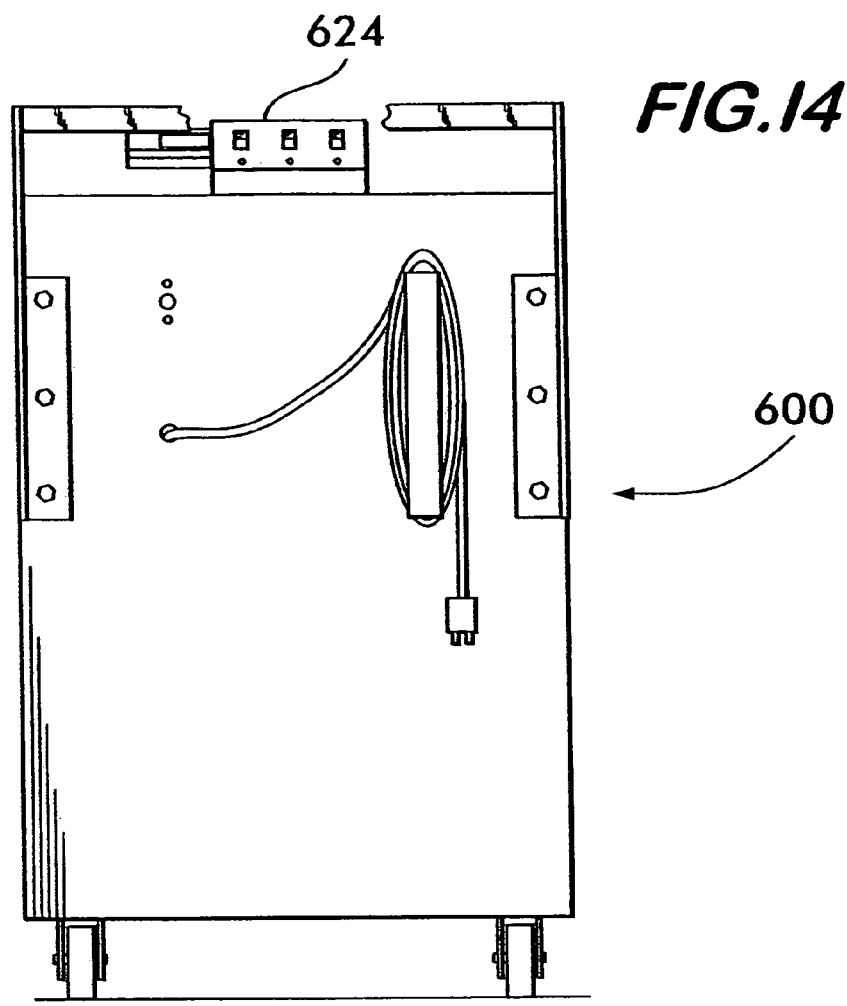
FIG. 14 is a rear view of the chemical neutralizing station of the present invention.

Referring now to FIGS. 13-14, there is shown the chemical neutralizing station 600 of the present invention. The chemical neutralizing station 600 is adapted for use with a reprocessing unit, such as the reprocessing unit 83, to perform several processes associated with the operation of the reprocessing unit 83. The station 600 can be made portable using a cart or any other vehicle known to those skilled in the art for permitting the elements of the chemical neutralizing station 600 to be conveniently moved to and from the vicinity of a reprocessor, a number of processors, a disposal location or any other area required in the maintenance of reprocessor devices.

The operations include operations such as filing a reprocessor reservoir 290 of the reprocessing unit 83, draining a reprocessor reservoir 290 as part of a refilling operation, sanitizing a reservoir 290, draining a reservoir 290 temporarily to permit work to be performed on the reprocessor unit 83, neutralizing the materials within the reprocessor reservoir 290 and sanitizing the reprocessor reservoir 290 by loading the reservoir 290 with disinfectant pumped from the chemical neutralizing station 600. In order to provide safety to users and the environment, the chemical neutralizing station 600 is adapted to form a substantially closed fluid transfer system in cooperation with the reservoir 290 for preventing the release of fumes during operations such as the foregoing.

The chemical processing station 600 is provided with a container such as a sealed chemical containment barrel 634 for containing fluids during the operation of the station 600 as well as for transportation and storage of materials between operations thereof if desired. During a disinfectant neutralizing operation performed for the purpose of neutralizing spent disinfectant materials in a reprocessing unit reservoir 290 for safe disposal, the chemical neutralizing station 600 can be wheeled to the vicinity of a reprocessing unit 83. In order to remove the spent disinfectant materials from the reservoir 290 of a reprocessor unit 83 the fitting 644 of the processing station 600 can be placed into fluid communication with the reservoir 290. The pump 650 can be activated to draw the disinfectant from the reservoir 290 by way of the conduit 646 and the conduit 654 into the sealed chemical containment barrel 634. The fluid materials in the conduit 654 are expelled from the orifice 674 of the fitting 678 into the interior of the containment barrel 634.

The distance of the fitting orifice 674 above the bottom 670 of the sealed chemical containment barrel 634 and the angle of the fitting 678 with respect to the bottom 670 are selected to cause the material propelled from the conduit 654 into the interior of the containment barrel 634 to swirl within the containment barrel 634. In one preferred embodiment of the invention, the orifice 674 at the bottom of the fitting 678 can be positioned approximately 5 to 7 inches above the bottom 670 of the containment barrel 634. Furthermore, in a preferred embodiment of the invention, the fitting 674 can be disposed at an angle approximately twenty to forty degrees with respect to the bottom 670. Advantageous results have been obtained by placing the fitting approximately 6 inches from the bottom with the fitting at an angle of approximately thirty degrees. However, it will be understood that those skilled in the art can place the orifice at any distance or any angle that will cause the propelled fluid to swirl a sufficient amount to dissolve and mix with a neutralizing chemical as described in more detail below. Preferably, the fitting having the orifice 674 is welded in place to prevent movement thereof.

In the preferred embodiment of the invention a powdered neutralizing chemical can be introduced into interior of the containment barrel 634 by way of a neutralizing input in order to prepare the material for safe disposal. The powdered neutralizing chemical can be poured into the containment barrel 634 simultaneously with the pumping of the fluid from the reprocessor reservoir 290 into the containment barrel 634 by the pump 650. A cap on the neutralizing input 616 can be unscrewed and the powdered neutralizer can be introduced to the top of the containment barrel 634 using a funnel. In one embodiment of the invention, the neutralizing powder can be glycene, preferably in combination with a buffer.

The swirling motion of the fluid within the containment barrel 634 caused by the motion of the fluid materials propelled from the orifice 674 can result in the powder introduced by way of neutralizing input 616 being mixed and dissolved in the fluid in order to facilitate the neutralization of the disinfectant material. In this manner, the dangers of performing the mixing manually are eliminated. There is no opportunity for the fluid being transferred and mixed to splash onto a user, and the user is not subjected to fumes from the mixture since the fluid transfer circuits between the reservoir 83 and the containment vessel 634 are substantially air tight. Furthermore, the total amount of time required to neutralize the fluid is decreased since the neutralization begins during the fluid transfer process.

In another embodiment of the invention a liquid neutralizing chemical can be introduced into the containment barrel 634. The liquid neutralizing chemical can be introduced by way of the liquid chemical input 612 which is provided at the top of the containment barrel 634. The previously described swirling motion of the materials propelled from the orifice 674 can mix the liquid neutralizing agent in the same manner as that previously described with respect to the mixing of the powder neutralizing chemical introduced by way of the input 616. The liquid neutralizing chemical entering the liquid chemical input 612 and the powdered neutralizer introduced by way of the neutralizing input 16 can be directed into the interior of the containment vessel 634 using a T-fitting 614 or any other suitable fitting. Furthermore, the inputs 612, 616 can be used for cleaning the containment barrel 634.

As the pump 650 propels the fluid into the interior of the containment barrel 634, the liquid level in the chemical containment barrel 634 rises and gas is forced out of the containment barrel 634 by way of the conduit 632. The gas leaving the containment barrel 634 by way of the conduit 632 can contain noxious or even toxic fumes. Therefore, in a preferred embodiment of the invention the gas conducted by way of the conduit 632 is passed through a charcoal filter canister 626 to remove any dangerous materials therein. Furthermore, a chemical overfill catch bowl 630 can be provided between the conduit 632 and the charcoal filter canister 626 in case fluid from the containment barrel 634 escapes into the conduit 632, for example, due to overfilling of the containment barrel 634. The chemical overfill catch bowl 630 thus prevents any liquid that may get into the conduit 632 from fouling the charcoal filter canister 626.

When emptying the sealed chemical containment barrel 634, the pump 662 can pull fluid from the containment barrel 634 by way of the conduit 666 and transmit the fluid by way of the conduit 658 through the fitting 656 to the exterior of the processing station 600. In this manner, materials such as neutralized disinfectant fluid can be removed from the chemical processing station 600 for disposal. Additionally, using the chemical neutralizing station 600, fluids from the reservoir 290 can be temporarily drained from the reservoir 290 to permit work to be performed on the reprocessing unit 83. The fluids can be drained from the reservoir 290 using the pump 650 as previously described. When it is time to load fluid into the reservoir 290 of the reprocessing unit 83, the reservoir 290 can be coupled in fluid communication with the fitting 644 and the pump 650 can be used to send the fluid back to the reservoir 290. Similarly, when neutralized fluid is emptied from the containment barrel 634 the fitting 644 can be coupled to a conduit for transmitting the fluid to an appropriate container or location for disposal. Furthermore, pump 662, along with the pump 650, can prevent backflow of the fluid.

In a preferred embodiment of the chemical neutralizing station 600 the bottom 670 of the chemical containment barrel 634 can be provided with a well 676 for collecting the fluid during draining thereof. The orifice of the fitting 672 that is coupled to the conduit 666 can be located inside the well 676. In a preferred embodiment the distance the orifice of the fitting 672 to the bottom of the well 676 is approximately one-sixteenth of an inch. This arrangement permits substantially complete draining of the chemical containment barrel 634. Under these circumstances the amount of noxious fluid remaining in the containment barrel 636 can be minimized and the contamination of any other materials subsequently pumped into the containment barrel 634 can be minimized.

An overfill safety float 638 can be provided to prevent overfilling of the sealed chemical containment barrel 634. Pumps 650, 662 can be turned off in response to detection of an overfill by the overfill safety float 638. A containment barrel level sight glass 652 can provide an opening such as a slit through a side cover (not shown) of the chemical neutralizing station 600. This permits visual monitoring of the level within the sealed chemical containment barrel 634. Additionally, a sight glass 628 can be provided through a side cover (not shown) of the chemical processing station 600 in order to permit visual monitoring the chemical over flow catch bowl 630. The containment barrel level sight glass 652 and the sight glass 628 can be graduated in order to facilitate monitoring of the operations of the station 600. A light can be provided within the neutralizing station 600 to project light through the sealed chemical containment barrel 634 and the over flow catch bowl 630 toward their respective sight glasses 628, 656 in order to facilitate visual monitoring of the operations of the station 600 through the sight glasses 628, 656.

Figure 15:
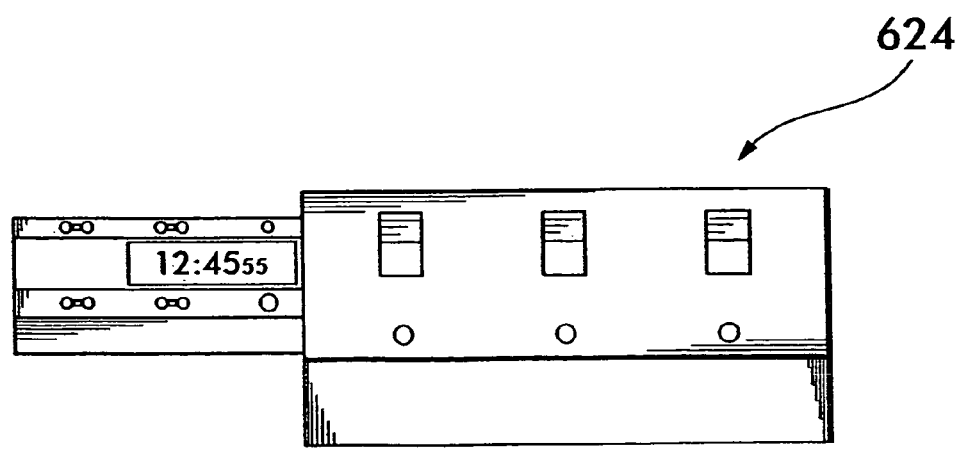
FIG. 15 is the control panel of the chemical neutralizing station of the present invention.
Figure 16:
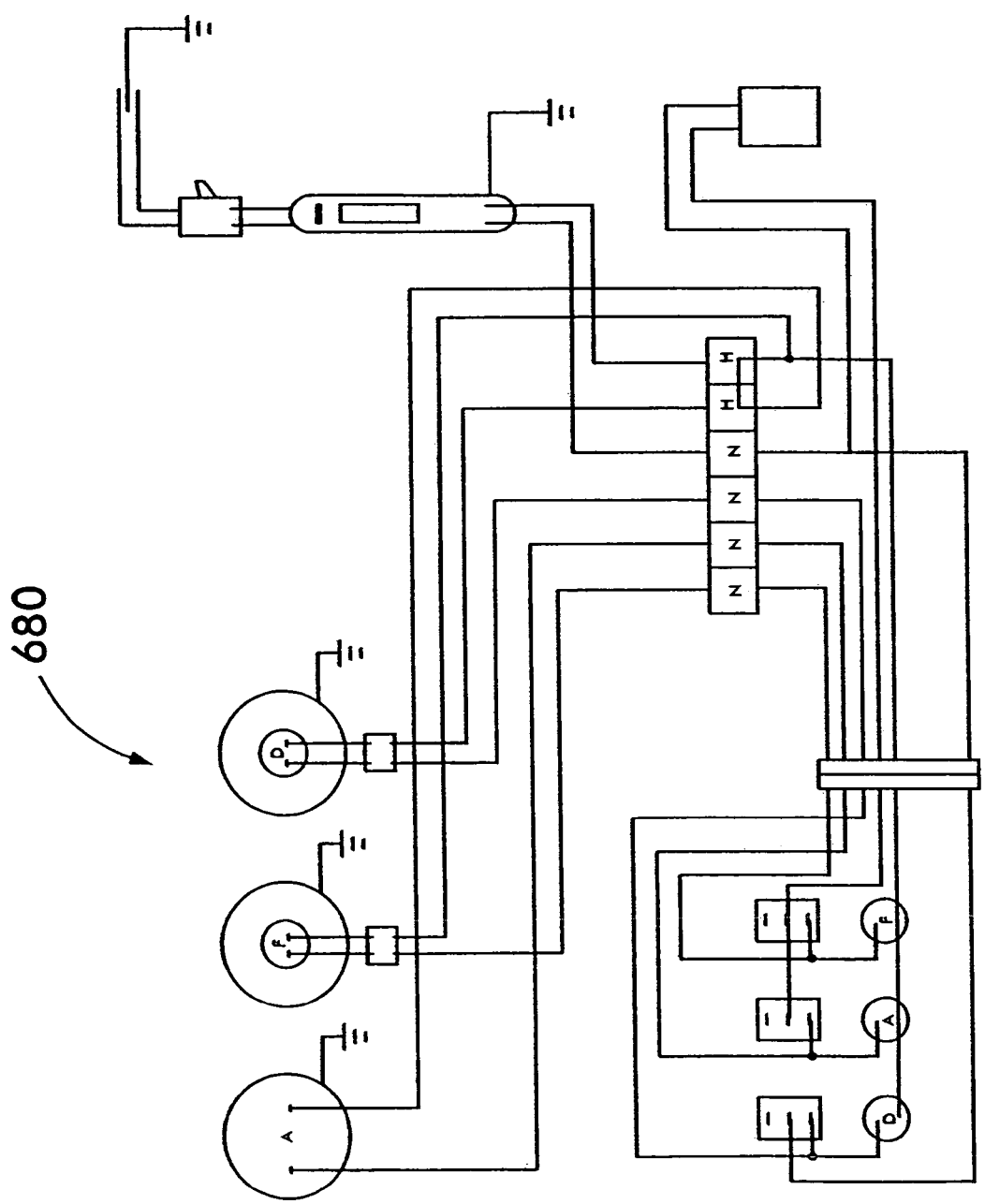
FIG. 16 is a schematic diagram of the circuitry for controlling the chemical neutralizing station of FIG. 13.

Referring now to FIGS. 14, 15, there is shown a control panel 624 and a schematic representation 680 of circuitry for controlling the operation of the chemical processing station 600. Using the switches on the control panel 624 and the circuitry represented by the schematic 680 one skilled in the art can control all elements of the chemical processing station 600 in order to perform operations with the cart 600 such as those described herein above. The control panel 624 can include a timer for timing the operations of the station 600, such as the neutralizing of the fluid from the reservoir 290. Additionally, it will be understood by those skilled in the art that the disinfectant transfer system of FIGS. 11 and 12 can be used in cooperation with the chemical processing station 600 to facilitate the maintenance of reprocessor systems such as the reprocessing unit 83. For example, the chemical processing station 600 can be used to withdraw disinfectant from the reservoir of a reprocessor unit 83 and the disinfectant transfer system of FIGS. 11 and 12 can be conveniently disposed upon the chemical processing station 600600 to transfer fresh disinfectant into the reservoir. Furthermore, it will be understood that the station 600 can be used for loading and draining any noxious or toxic fluids, for example, loading and draining antifreeze for radiators, oil or laboratory chemicals.

Without further elaboration, the foregoing will so fully illustrate the invention that others may, by applying current or future knowledge readily adapt the same for use under the various conditions of service.

What is claimed is:

1. A method for handling a noxious disinfectant fluid releasing a noxious gas stored within a reprocessor reservoir of a reprocessor for reprocessing medical equipment having internal passageways, comprising:

providing a sealed container having a container bottom on a portable disinfectant transfer vehicle for containing said disinfectant fluid and preventing escape of said disinfectant fluid and capturing and treating said noxious gas with a carbon filter while containing said disinfectant fluid to provide a sealed portable container;

performing first, second and third procedures on said reprocessor using said portable disinfectant transfer vehicle;

wherein said first procedure includes providing fresh disinfectant fluid to said reprocessor reservoir comprising;

(i) disposing said fresh disinfectant fluid within said sealed portable container at a location remote from said reprocessor using a portable input pump coupled to said portable disinfectant transfer vehicle;

(ii) transporting said sealed portable container containing said fresh disinfectant fluid to a vicinity of said reprocessor; and (iii) pumping said fresh disinfectant fluid from said sealed portable container into said reprocessor reservoir using a portable output pump coupled to said portable disinfectant transfer vehicle;

wherein said second procedure includes performing maintenance on said reprocessor comprising;

(i) pumping said disinfectant fluid from said reprocessor reservoir into said sealed portable container using said portable input pump to provide a pumped disinfectant fluid;

(ii) performing said maintenance on said reprocessor; and (iii) pumping said pumped disinfectant fluid from said sealed portable container into said reprocessor reservoir after said maintenance is performed using said portable output pump;

wherein said third procedure includes disposing of spent disinfectant fluid stored in said reprocessor reservoir comprising;

(i) positioning a conduit fitting at a predetermined distance and a nonorthogonal angle with respect to said bottom of said sealed portable container, said predetermined distance and said nonorthogonal angle being selected to produce a swirling motion of fluid pumped into said sealed portable container;

(ii) pumping said spent disinfectant fluid from said reprocessor reservoir through said conduit fitting into said sealed portable container using said portable input pump;

(iii) receiving a neutralizing chemical into said sealed portable container through an opening at the top of said sealed portable container independently of any pumping of said neutralizing chemical and simultaneously with said pumping of said spent disinfectant fluid to provide a simultaneously introduced unpumped neutralizing chemical;

(iv) mixing said simultaneously introduced unpumped neutralizing chemical with said spent disinfectant fluid using said swirling motion whereby said simultaneously introduced unpumped neutralizing chemical and said spent disinfectant fluid are mixed without pumping of said neutralizing chemical and without release of said noxious gas from said sealed portable container to produce a neutralized solution;

(v) transporting said neutralized solution using said portable disinfectant transfer vehicle from said vicinity of said reprocessor reservoir to a disposal location having a disposal conduit for receiving said neutralized solution remote from said reprocessor reservoir; and (vi) pumping said neutralized solution from said sealed portable container through said disposal conduit using said portable output pump.

2. The method of claim 1, wherein said conduit fitting is positioned between approximately five inches and approximately seven inches from said bottom of said sealed portable container to mix said simultaneously introduced neutralizing chemical with said spent disinfectant fluid.

3. The method of claim 1, wherein said conduit fitting is positioned at an angle between approximately twenty degrees and approximately forty degrees with respect to said bottom of said sealed portable container to mix said simultaneously introduced neutralizing chemical with said spent disinfectant fluid.

4. The method of claim 1, wherein said conduit fitting is positioned at an angle of approximately thirty degrees with respect to said bottom of said sealed portable container to mix said simultaneously introduced neutralizing chemical with said spent disinfectant fluid.

* * * * *